(12) United States Patent
Wilson et al.

(10) Patent No.: US 7,999,232 B2
(45) Date of Patent: Aug. 16, 2011

(54) GAS DETECTOR

(75) Inventors: Andrew Colin Wilson, Dunedin (NZ);
Sri Kumar Sandeep, Dunedin (NZ);
Reece Wim Geursen, Dunedin (NZ)

(73) Assignee: Photonic Innovations Limited, Dunedin (NZ)

( * ) Notice: Subject to any disclaimer, the term of this patent is extended or adjusted under 35 U.S.C. 154(b) by 0 days.

(21) Appl. No.: 12/520,687

(22) PCT Filed: Dec. 21, 2007

(86) PCT No.: PCT/NZ2007/000391
§ 371 (c)(1),
(2), (4) Date: Feb. 26, 2010

(87) PCT Pub. No.: WO2008/079032
PCT Pub. Date: Jul. 3, 2008

(65) Prior Publication Data
US 2010/0140478 A1    Jun. 10, 2010

Related U.S. Application Data

(60) Provisional application No. 60/871,466, filed on Dec. 22, 2006.

(51) Int. Cl.
*G01N 21/35* (2006.01)
(52) U.S. Cl. .................................. 250/339.13
(58) Field of Classification Search ............... 250/338.1, 250/339.07, 339.12, 339.13, 343
See application file for complete search history.

(56) References Cited

U.S. PATENT DOCUMENTS

| 4,516,432 A | 5/1985 | Hironaga et al. |
| 4,824,251 A | 4/1989 | Slotwinski et al. |
| 4,914,719 A | 4/1990 | Conlon et al. |
| 5,384,640 A | 1/1995 | Wong |
| 6,050,656 A | 4/2000 | Farahi et al. |
| 6,091,504 A | 7/2000 | Walker et al. |
| 6,509,567 B2 | 1/2003 | Boudet et al. |

(Continued)

FOREIGN PATENT DOCUMENTS
EP    0364642    4/1990
(Continued)

OTHER PUBLICATIONS

M. Kroll et al., "Measurement of gaseous oxygen using diode laser spectroscopy," Appl. Phys. Lett. 51 (18), Nov. 2, 1987, pp. 1465-1467.

(Continued)

*Primary Examiner* — David P Porta
*Assistant Examiner* — Marcus H Taningco
(74) *Attorney, Agent, or Firm* — Dann, Dorfman, Herrell and Skillman, P.C.

(57) ABSTRACT

A gas detector (10) that is arranged to sense the concentration levels of target gases oxygen, methane, carbon monoxide, and hydrogen sulphide, within a gas sample from an environment surrounding the detector. The gas detector (10) comprises laser sources (12a-12d) that are arranged to transmit radiation through the gas sample at four target wavelengths that correspond approximately to the optimum absorption wavelengths of each of the target gases and an optical detector (16) that is arranged to sense the intensity of the radiation transmitted through the gas sample at each of the target wavelengths. A control system (22) generates representative concentration level information for the target gases based on the level of absorption of the radiation transmitted.

30 Claims, 19 Drawing Sheets

U.S. PATENT DOCUMENTS

| | | |
|---|---|---|
| 7,005,645 B2 | 2/2006 | Von Drasek et al. |
| 7,034,325 B2 | 4/2006 | Besesty et al. |
| 2002/0036266 A1* | 3/2002 | Dreyer et al. ............... 250/345 |
| 2006/0088068 A1* | 4/2006 | Farrell et al. ............. 372/29.02 |
| 2006/0098202 A1 | 5/2006 | Willing et al. |
| 2006/0158644 A1 | 7/2006 | Silver |
| 2006/0180763 A1 | 8/2006 | Yoshida et al. |
| 2006/0232772 A1 | 10/2006 | Silver |
| 2007/0291271 A1 | 12/2007 | Wu et al. |

FOREIGN PATENT DOCUMENTS

| | | |
|---|---|---|
| EP | 0447931 | 9/1991 |
| FR | 2666163 | 2/1992 |
| GB | 2411953 | 9/2005 |
| JP | 9-282577 | 10/1997 |
| JP | 2001-159605 | 6/2001 |
| WO | 02/50515 | 6/2002 |
| WO | 03/062801 | 7/2003 |
| WO | 03/069316 | 8/2003 |
| WO | 2005/088275 | 9/2005 |

OTHER PUBLICATIONS

International Search Report, PCT/NZ2007/000391, mailed Jun. 26, 2008.

* cited by examiner

GAS DETECTOR

CROSS REFERENCE TO RELATED APPLICATION

This application claims the benefit of U.S. Provisional Application No. 60/871,466, filed Dec. 22, 2006.

FIELD OF THE INVENTION

The present invention relates to a gas detector for sensing the concentration of multiple target gases in an environment. In particular, although not exclusively, the environment is a confined space or other such space where the target gases may congregate/concentrate.

BACKGROUND TO THE INVENTION

Various types of gas detectors are available, including catalytic bead (pellistor) gas detectors, electrochemical cell based gas detectors, photo-ionisation gas detectors, and laser spectroscopy gas detectors, such as laser diode spectroscopy (LDS) gas detectors for example.

LDS gas detectors utilise laser diodes that transmit radiation at wavelengths that correspond to the optical absorption lines of the target gases being detected in the environment. An optical detector senses the radiation that is transmitted through a gas sample of the environment so that the concentration or quantity of the target gas can be determined based on the intensity of the radiation received with the target gas present and the transmitted intensity without the target gas. One such LDS gas detector design is described in international PCT patent application publication WO 2005/088275.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide a gas detector for sensing the concentration of multiple target gases within a gas sample from a surrounding environment, or to at least provide the public with a useful choice.

SUMMARY OF THE INVENTION

In a first aspect, the present invention broadly consists in a gas detector that is arranged to sense the concentration levels of target gases oxygen, methane, carbon monoxide, and hydrogen sulphide, within a gas sample from an environment surrounding the detector, comprising: a laser source or sources that is/are arranged to transmit radiation through the gas sample at four target wavelengths that correspond approximately to the optimum absorption wavelengths of each of the target gases; an optical detector or detectors that are arranged to sense the intensity of the radiation transmitted through the gas sample at each of the target wavelengths; and a control system that is arranged to operate the laser source(s) and optical detector(s), and which generates representative concentration level information relating to each of the target gases within the gas sample based on the level of absorption of the radiation transmitted into the gas sample at each of the target wavelengths.

Preferably, the control system is arranged to determine direct absorption levels based on the intensity of the radiation received by the optical detector(s) relative to the intensity of the radiation transmitted by the laser source(s) at each of the target wavelengths.

Preferably, the laser source(s) are arranged to transmit radiation in the infrared band. In one form, the laser source(s) are arranged to transmit radiation in the wavelength range of between about 760 nm and about 1700 nm. In another form, the laser source(s) are arranged to transmit the radiation in the wavelength range of between about 2 μm and about 6 μm.

Preferably, the laser source(s) are laser diodes(s).

In one form, the gas detector comprises four laser sources, each of which is arranged to transmit radiation at one of the target wavelengths corresponding to one of the target gases. Preferably, each of the four laser sources are laser diodes of either vertical-cavity surface-emitting laser (VCSEL) or distributed feedback laser (DFB) type.

In one form, the four laser sources comprise one VCSEL laser diode that is arranged to transmit radiation at the target wavelength corresponding to oxygen and three DFB laser diodes that are arranged to transmit radiation at the respective target wavelengths of methane, carbon monoxide, and hydrogen sulphide. In another form, the four laser sources comprise four VCSEL laser diodes that are arranged to transmit radiation at the respective target wavelengths of oxygen, methane, carbon monoxide and hydrogen sulphide.

In one form, the gas detector comprises a single optical detector that is arranged to sense the intensity of radiation transmitted through the gas sample at all of the target wavelengths of the target gases.

In another form, the gas detector comprises a first optical detector that is arranged to sense the intensity of radiation transmitted through the gas sample at the target wavelength of methane, carbon monoxide and hydrogen sulphide, and a second optical detector that is arranged to sense the intensity of the radiation transmitted through the gas sample at target wavelength of oxygen. Preferably, the first optical detector is a germanium (Ge) photodiode and second optical detector is a silicon (Si) photodiode.

Preferably, the optical detector(s) are photodiode(s).

In one form, the control system comprises a single current driver for driving the laser source(s). Preferably, there are four laser sources, each of which is arranged to transmit radiation at one of the target wavelengths corresponding to one of the target gases, and wherein the single current driver is arranged to drive all four laser sources.

In another form, there are four laser sources, each of which is arranged to transmit radiation at one of the target wavelengths corresponding to one of the target gases, and wherein the control system comprises a plurality of current drivers, each current driver driving one or more of the four laser sources.

Preferably, the laser source(s) are driven by one or more current drivers.

In one form, the control system is arranged to operate the current driver(s) to activate all laser sources concurrently and continuously. Preferably, the current driver(s) of the control system are arranged to drive the laser source(s) with continuous drive currents.

In another form, the control system is arranged to control the current driver(s) to activate each laser source sequentially in a pre-determined pattern in a cyclical manner one at a time. Preferably, the current driver(s) of the control system are arranged to drive the laser source(s) in a pre-determined pattern via pulsed drive currents.

Preferably, the current driver(s) of the control system are arranged to drive the laser source(s) using drive currents that are modulated with a sine wave and a triangle wave such that the signals are simultaneously triangularly ramped and sinusoidally modulated. More preferably, the current driver(s) of the control system are arranged to generate current drive signals in the form of pulses that are triangularly ramped and sinusoidally modulated.

Preferably, the control system further comprises a lock-in amplifier or amplifiers that are arranged to amplify or filter an output intensity signal from the optical detector(s) at each of the target wavelengths of the target gases.

In one form, the gas detector comprises a single optical detector and wherein the control system comprises a single lock-in amplifier that is operated to amplify and filter the output intensity signal from the optical detector at each of the target wavelengths, one target wavelength at a time to correspond with radiation wavelengths transmitted by the laser source(s).

Preferably, the control system further comprises a temperature control module or modules that are arranged to sense and control the operating temperature(s) of the laser source(s). More preferably, the temperature control module(s) are arranged to maintain the operating temperature of the laser source(s) at pre-determined temperature(s) that are required for transmission of radiation at the target wavelengths.

Preferably, there are four laser sources and four independent temperature control modules, one for each laser source.

Preferably, the gas detector further comprises a gas space through which a gas sample from the environment may pass, the laser source(s) and optical detector(s) being arranged about the gas space such that the laser source(s) transmit radiation through the gas space for detection by optical detector(s).

Preferably, the radiation at one or more of the target wavelengths is transmitted from the laser source(s) directly through the gas space to the optical detector(s).

Preferably, the laser source(s) transmitting radiation at the target wavelengths of oxygen and methane are arranged to transmit the radiation directly through the gas sample to the optical detector(s).

Preferably, the radiation transmission path length between the laser source transmitting at the target wavelength of oxygen and the optical detector(s) is in the range of about 0.01 m to about 0.1 m. More preferably, the radiation transmission path length between the laser source transmitting at the target wavelength of oxygen an the optical detector(s) is approximately 0.05 m.

Preferably, the radiation transmission path length between the laser source transmitting at the target wavelength for methane and the optical detector(s) is in the range of about 0.05 m to about 0.2 m. More preferably, the radiation transmission path length between the laser source transmitting at the target wavelength of methane and the optical detector(s) is approximately 0.1 m.

Preferably, the gas space comprises an optical system and wherein the radiation at one or more of the target wavelengths is indirectly transmitted from the laser source(s) to the optical detector(s) via the optical system, the optical system being arranged to modify and increase the radiation transmission path length at those target wavelengths relative to a direct transmission through the gas space.

Preferably, the laser source(s) transmitting at the target wavelengths of carbon monoxide and hydrogen sulphide are arranged to direct the radiation indirectly to the optical detector(s) via the optical system.

Preferably, the radiation transmission path length from the laser source transmitting at the target wavelength of carbon monoxide and the optical detector(s), after transmission through the optical system, is in the range of about 20 m to about 50 m. More preferably, the radiation transmission path length between the laser source transmitting at the target wavelength of carbon monoxide and the optical detector(s), after transmission through the optical system, is approximately 30 m.

Preferably, the radiation transmission path length from the laser source transmitting at the target wavelength of hydrogen sulphide and the optical detector(s), after transmission through the optical system, is in the range of about 10 m to about 35 m. More preferably, the radiation transmission path length from the laser source transmitting at the target wavelength of hydrogen sulphide and the optical detector(s), after transmission through the optical system, is approximately 20 m.

Preferably, the optical system in the gas space comprises a multi-pass cell having an input aperture through which radiation from the laser source(s) enters the cell and an output aperture through which the radiation exits the cell for detection by the optical detector(s), the cell further comprising reflecting surfaces that are arranged to reflect the radiation back and forth within the cell multiple times to extend the radiation transmission path length through the gas sample within the cell before the radiation exits the cell through the output aperture.

Preferably, the multi-pass cell of the optical system comprise two spaced-apart reflecting surfaces that are arranged to reflect the radiation entering the cell through the input aperture back and forth between the surfaces multiple times before directing the radiation to exit the cell through the output aperture.

In one form, the reflecting surfaces of the multi-pass cell are planar mirrors.

In another form, the reflecting surfaces of the multi-pass cell are curved mirrors. The curved mirrors of the multi-pass cell may be in the form of spherical concave mirrors. Alternatively, the curved mirrors of the multi-pass cell may be in the form of cylindrical concave mirrors.

Preferably, the input and output apertures of the multi-pass cell of the optical system may be the same aperture of separate apertures.

Preferably, the multi-pass cell of the optical system is arranged to receive two or more radiation beams at two or more of the target, wavelengths.

Preferably, the multi-pass cell of the optical system is arranged to reflect the radiation within the cell in a zig-zagged path in the cell before directing the radiation to exit the cell via the output aperture.

Preferably, the gas detector is in the form of a hand-held device having a housing within which the components are securely mounted and an aperture within the housing through which the gas sample from the environment may flow.

Preferably, the control system further comprises an output display for displaying the concentration levels of the target gases within the sample.

Preferably, the control system comprises an alarm or alarms that are arranged to automatically trigger should the concentration levels of one or more of the target gases within the gas sample rise above or fall below predetermined maximum and minimum thresholds, the alarm(s) being any one or more of the following types: audible, visual, and/or tactile.

Preferably, the target wavelength transmitted for detecting oxygen is in the range of about 760 nm to about 766 nm. More preferably, the target wavelength transmitted for detecting oxygen is approximately 764 nm.

Preferably, the target wavelength transmitted for detecting carbon monoxide is in the range of about 1560 nm to about 1600 nm. Mote preferably, the target wavelength transmitted for detecting carbon monoxide is approximately 1565 nm.

Preferably, the target wavelength transmitted for detecting methane is in the range of about 1630 nm to about 1670 nm. More preferably, the target wavelength transmitted for detecting methane is approximately 1665 nm.

Preferably, the target wavelength transmitted for detecting hydrogen sulphide is in the range of about 1560 nm to about 1600 nm. More preferably, the target wavelength transmitted, for detecting hydrogen sulphide is approximately 1576 nm.

In a second aspect, the present invention broadly consists in a gas detector that is arranged to sense the concentration levels of a plurality of target gases within a gas sample from an environment surrounding the detector, comprising: a laser source or sources that is/are arranged to transmit radiation through the gas sample at target wavelengths that correspond approximately to the optimum absorption wavelengths of each of the target gases; an optical detector or detectors that are arranged to sense the intensity of the radiation transmitted through the gas sample at each of the target wavelengths; and a control system that is arranged to operate the laser source(s) and optical detector(s), and which generates representative concentration level information relating to each of the target gases within the gas sample based on the level of absorption of the radiation transmitted into the gas sample at each of the target wavelengths.

Preferably, the target gases may comprise any two or more of the target gases: oxygen, methane, carbon monoxide, hydrogen sulphide, ammonia, water, acetylene, carbon dioxide, nitrogen oxide, ethylene, and nitrogen dioxide.

The second aspect of the invention may comprise any one or more of the features outlined above in respect of the first aspect of the invention.

The term "gas sample" is intended to cover any volume of gas or mixture of gases, typically air, from the environment surrounding the gas detector.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

Figure 1:
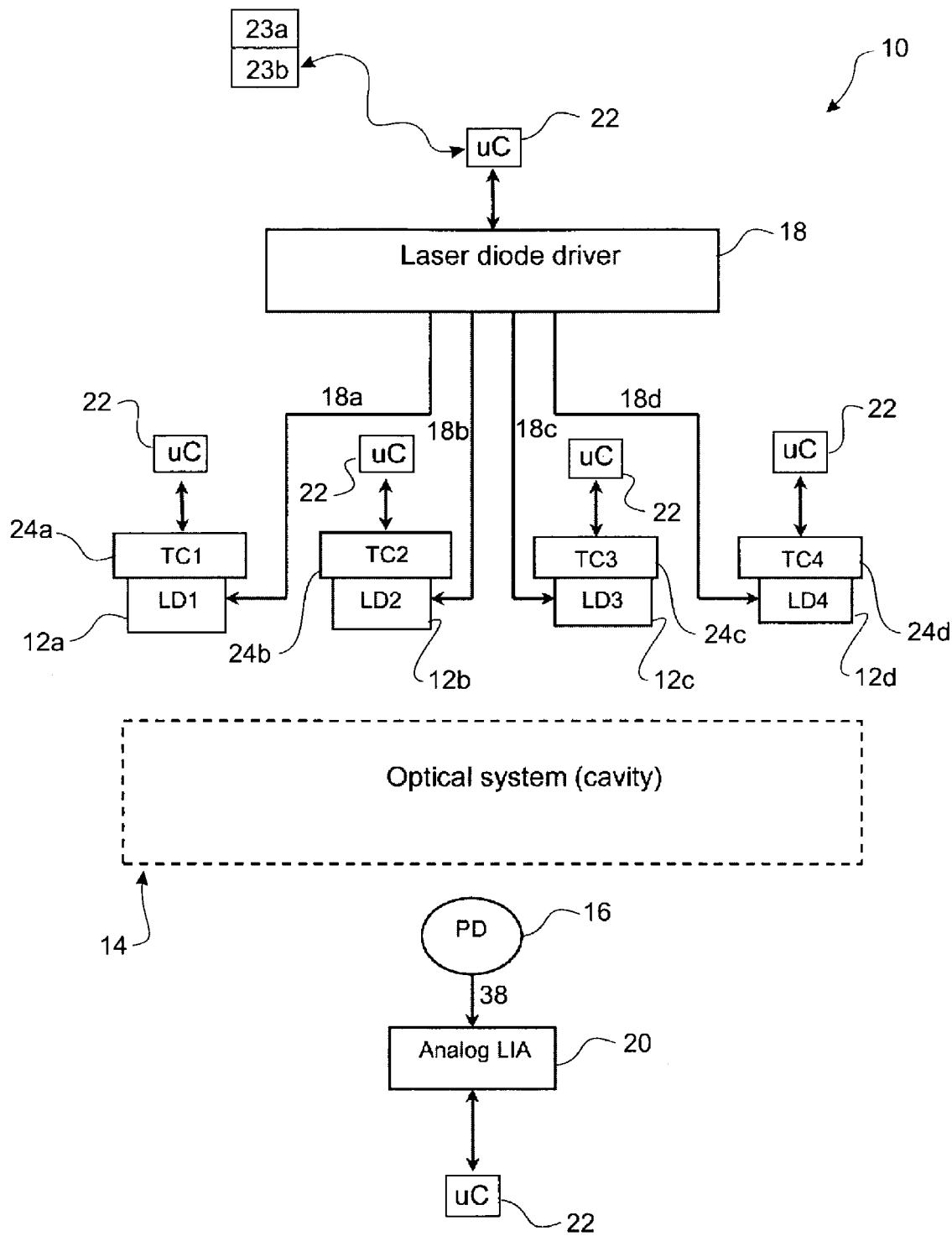
FIG. 1 is a schematic diagram of a first preferred form gas detector of the invention.

The present invention relates to a gas detector for sensing and determining representative concentrations or quantity levels of multiple target gases within an environment. In particular, the gas detector is arranged to sense a plurality of target gases in a gas sample from the environment surrounding the detector. The target gases may comprises any two or more of the following gases: oxygen, carbon monoxide, methane, hydrogen sulphide, ammonia, water, acetylene, carbon dioxide, hydrogen cyanide, chlorine, ethylene, methyl bromide, nitrogen oxide, and nitrogen dioxide, or any gas that has suitable absorption features in the infrared band. The concentration levels of the target gases are determined using laser spectroscopy. This involves directing electromagnetic radiation, such as infrared light, through the gas sample at specific target wavelengths that correspond approximately to determined optimum absorption wavelengths for each of the target gases and then sensing the intensity of the radiation transmitted through the gas sample at each of the target wavelengths. Representative concentration levels for each target gas in the gas sample may then be calculated based on the level of absorption of the radiation transmitted into the gas sample at each of the target wavelengths. As mentioned, the electromagnetic radiation may be in the infrared band. By way of example, the radiation may be in the wavelength range of 760-1700 nm, or alternatively in the wavelength range of 2-6 μm, or any other suitable range in the infrared band.

The gas detector is preferably portable and hand-held such that it may be carried by a user that is working in a confined space that may potentially contain, or be subject to, a build-up of hazardous gases, such as carbon monoxide, methane, hydrogen sulphide, ammonia and the like, or a diminished supply of breathable oxygen or a dangerously high oxygen concentration that presents an explosive risk. In operation, the gas detector is arranged to interrogate a gas sample within the surrounding environment to assess the concentration levels, for example parts-per-million (ppm) levels of the target gases with respect to air or another gas within the environment, and continuously display those levels to the user. Additionally or alternatively, the gas detector may be arranged to compare the sensed concentration levels with predetermined maximum or minimum threshold levels and alerts the user, via an audible and/or visual and/or tactile alarm or alarms, should a breach of the threshold levels occur. For example, the alarm of the gas detector may be triggered if the concentration levels of carbon monoxide, methane, hydrogen sulphide or ammonia exceed maximum preset thresholds that may pose a danger to a user. Likewise, the alarm(s) may be triggered if the oxygen concentration level declines below a minimum preset threshold such that a user may not be able to safely breathe within the environment or if the concentration level increases to a point that presents an explosive risk.

First Preferred Form Gas Detector

Referring to FIG. 1, a schematic diagram of a first preferred form gas detector 10 is shown. The gas detector 10 is arranged to sense the concentration levels of four target gases, namely oxygen, carbon monoxide, methane and hydrogen sulphide. Four laser sources 12a-12d are provided that are arranged to transmit radiation at four target wavelengths corresponding to the four target gases through a gas space 14 that contains a gas sample from the surrounding environment and an optical detector 16 is provided for sensing the intensity of the radiation transmitted through the gas sample at each target wavelength. The gas detector 10 also comprises a control system that operates and coordinates the laser sources 12a-12d and optical detector 16 and which processes the detected intensity levels of the radiation emanating from the gas sample to generate representative concentration level information in relation to each of the four target gases based on the absorption levels. Various methods of calculating concentration level information based on absorption levels are known to a skilled person in the art of laser spectroscopy. Some of these calculation techniques will be described below but it will be appreciated that other known techniques may also be utilised.

In the first preferred form, the four laser sources 12a-12d are each arranged to transmit infrared radiation at one of the target wavelengths corresponding to an optimum selected absorption wavelength of one of the target gases. In particular, each laser source has a different wavelength specific to the gas it is targeting. By way of example, Table 1 below summarises which laser source 12a-12d relates to which target gas and the associated approximate transmission wavelength, by way of example only. The target wavelengths may be set at the maximum absorption wavelengths for the target gases, although other wavelengths may be more suitable. Various factors are taken into account when determining the target wavelengths, including the likely concentration levels, gas absorption characteristics (for example, line intensity), radiation path length, system noise, interference from other gases, and other such factors. The selected target wavelengths are a compromise between these things.

TABLE 1

| Laser Source | Target Gas | Target Radiation Wavelength Range, and Preferable Wavelengths |
| --- | --- | --- |
| 12a | Oxygen | 760 nm-766 nm, preferably 764 nm |
| 12b | Carbon Monoxide | 1560 nm-1600 nm, preferably 1565 nm |
| 12c | Methane | 1630 nm-1670 nm, preferably 1665 nm |
| 12d | Hydrogen Sulphide | 1560 nm-1600 nm, preferably 1576 nm |

In the first preferred form, the laser sources 12a-12d are laser diodes, such as vertical-cavity surface-emitting lasers (VCSELs) or distributed feedback lasers (DFBs), and the optical detector 16 is a suitable photodiode for sensing radiation transmitted for the particular laser diode.

Upon exiting the gas space 14, the radiation from laser diodes 12a-12d is detected by an optical detector, such as a photodiode 16. In operation, the control system of the gas detector 10 is arranged to measure a harmonic of the photodiode 16 output and from this extract the absorption level for each of the target wavelengths transmitted by the laser diodes 12a-12d. This measured absorption level of the gas sample at each wavelength is proportional to the concentration levels of the target gases in the gas sample. Therefore, the measured harmonic of the intensity, at each target wavelength, can be processed to generate corresponding target gas concentration levels in a manner well known to those skilled in the art of laser spectroscopy. Broadly speaking there are two methods for calculating the concentration. The first one uses a sample of the gas of interest with known characteristics to calibrate the measurement device (gas detector). The second method is based on knowledge of: the gas's absorption properties, path length, pressure, and temperature. It uses either the signal peak height or a line shape fit of the signal to extract the required values for the concentration calculation.

In the first preferred form, the control system of the gas detector comprises a number of modules or subsystems. In particular, the control system comprises a main controller 22, for example a programmable microcontroller or microprocessor, current driver 18, lock-in amplifier 20, and temperature control modules 24a-24d. The control system may also comprise a liquid crystal display (LCD) or other output display, user interface, temperature sensor, pressure sensor, lower explosive limit (LEL) sensor, thermistor, multitone audible alarm, vibration alarm module, and photodiode signal processing circuits. In the first preferred form, the main controller 22 interfaces with and controls the current driver 18 associated with the laser diodes 12a-12d and the lock-in amplifier 20 associated with the photodiode 16. The main controller 22 of the control system also interfaces and controls the temperature control modules 24a-24d associated with each of the laser diodes 12a-12d. Main controller controls and coordinates all the subsystems. This includes controlling the generation of modulation signals, time management and signal processing.

In operation, the main controller 22 of the control system is arranged to receive and process the radiation intensity signals sensed by the photodiode 16, preferably after amplification and filtering by the lock-in amplifier 20, to generate representative concentration level information for each of the target gases. In particular, main controller 22 is arranged to analyse a particular harmonic intensity signal at each of the four target wavelengths and then generates representative concentration level information for each target gas based on the harmonic signal at each respective target wavelength in a manner that has been previously described.

The control system may also comprise a user interface 23*a* and output display 23*b* associated with the main controller 22. In particular, the output display may be arranged to display the representative concentration levels, for example in ppm levels, for each of the target gases on a display screen, such as a liquid crystal display (LCD), electronic ink, LED based display or the like. Additionally, the main controller 22 of the control system may be arranged to compare the representative concentration levels with preset maximum or minimum thresholds, time weighted averages (TWA), and short time exposure limits (STEL) associated with each of the target gases and activate an audible alarm via a buzzer and/or a visual alarm via the display and/or a tactile alarm via a vibration module for the user should the levels of any of the target gases breach those thresholds. TWA is time weighted average and is the recommended limit a person can be exposed to a particular gas over a period of time without causing harm. There are usually two time periods: 8 hour exposure and a 15 minute short term exposure limit (STEL).

For example, the main controller 22 may be preset with predetermined maximum threshold, TWA, and STEL concentration levels for hazardous gases carbon monoxide, methane, and hydrogen sulphide. Likewise, the main controller 22 may be provided with a preset maximum threshold concentration level for oxygen for alerting the user to an explosive risk and additionally a minimum preset threshold concentration level for oxygen to ensure the user can breathe safely within the environment. The control system may also have associated internal or external memory, such as flash memory or any other type of non-volatile memory, for storing data and input/output ports, for example a universal serial bus (USB) for transferring data in relation to the concentration level information for the target gases. Additionally, the gas detector 10 may also incorporate temperature and pressure sensors for sensing temperature and pressure within the environment for displaying to the user. The sensed temperature and pressure levels may also be utilised by the main controller 22 during the gas concentration level calculations to reduce errors and enhance accuracy. Further, the gas detector may also comprise a lower explosive level (LEL) sensor or sensors to provide an indication as to whether explosions are likely within the environment due to particular vapour levels or concentrations. As mentioned, the gas detector 10 is preferably portable and hand-held and will comprise power supply circuitry, a rechargeable battery and battery charging circuitry.

In the first preferred form, the laser diodes 12*a*-12*d* are sequentially operated in a cycle to transmit radiation one at a time by a single current driver 18 of the control system. Further, the control system includes a lock-in amplifier 20 that amplifies and filters the intensity output signal from the photodiode 16, with the lock-in amplifier parameters determined by the laser diode that is operating. In particular, the current driver 18 pulses each laser diode 12*a*-12*d* on and then off in a sequential manner one at a time in a predetermined pattern and then repeats the sequential cycle. In a synchronous manner, the lock-in amplifier 20 is arranged to sequentially filter and amplify the intensity output signals from the photodiode 16 for the target wavelength corresponding to whichever laser 12*a*-12*d* is operating for final processing by the main controller 22 of the control system. In the first preferred form, the current driver 18 and lock-in amplifier 20 are controlled and operated by the main controller 22 of the control system.

It will be appreciated that the laser diodes 12*a*-12*d* maybe operated in any predetermined pattern. For example, each laser diode 12*a*-12*d* may be operated one at a time in a sequence from left to right or specific laser diodes for particular target gases may be operated in a particular preset order. It will also be appreciated that each cycle of the pattern may also include skipping operation of one or more of the laser diodes for particular target gases. For example, the laser diodes 12*b*-12*d* for detecting target gases carbon monoxide, methane and hydrogen sulphide may be operated in a predetermined order every cycle but laser diode 12*a* for detecting oxygen may only be operated every tenth cycle. The reason for this is that the concentration level of oxygen in most environments is likely to be more stable relative to the other gases and therefore its detection every cycle may not be necessary.

Figure 2:
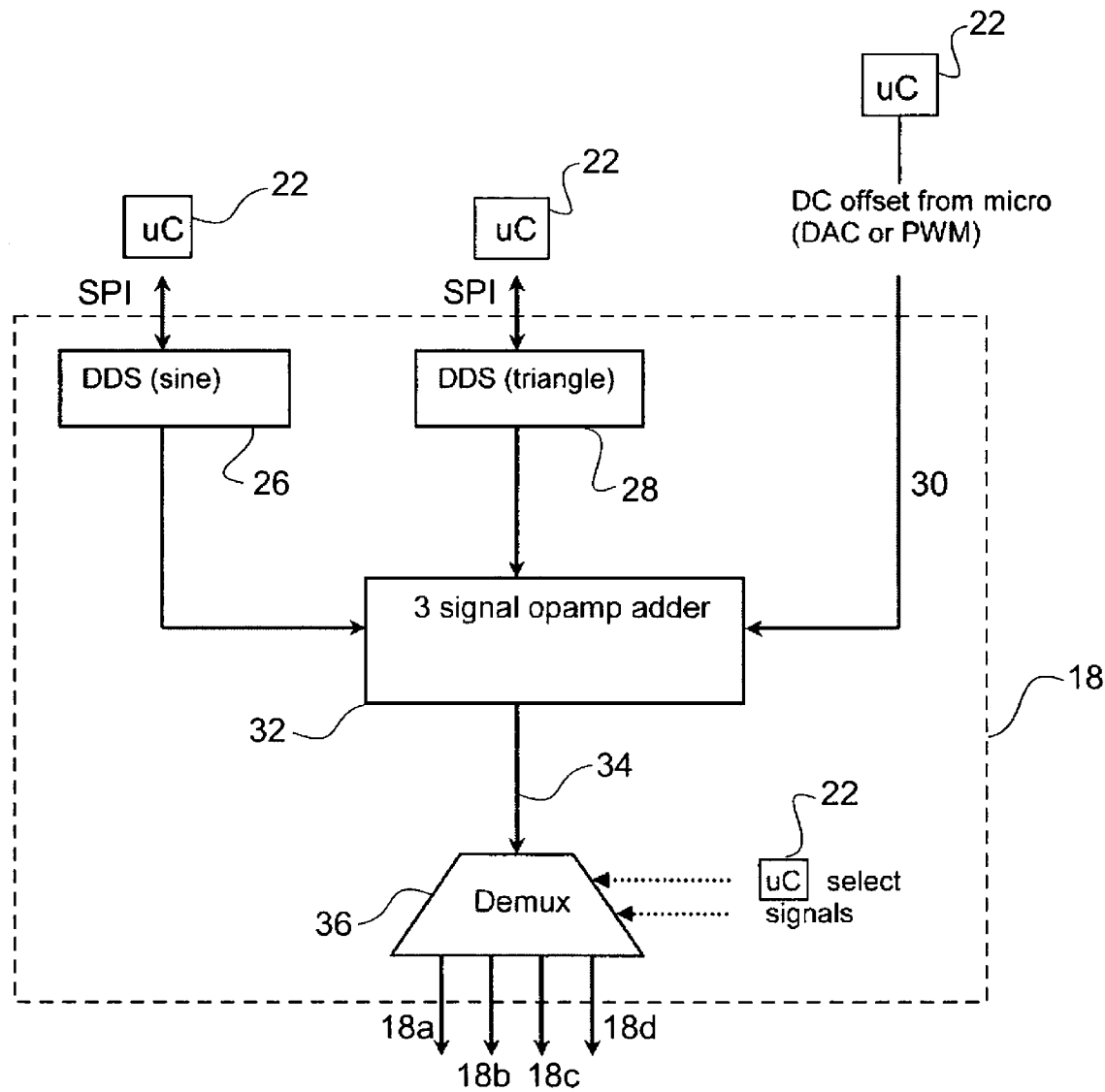
FIG. 2 is a schematic diagram of the current driver for the laser sources of the first preferred form gas detector.

Referring to FIG. 2, an expanded schematic diagram of the first preferred form single current driver 18 of the gas detector 10 is shown. As mentioned, the gas detector 10 preferably implements a pulsed current driving scheme to sequentially operate each of the laser diodes 12*a*-12*d* one at a time in a repeating cycle. Therefore, at any time only one of the laser diodes 12*a*-12*d* will be switched on and transmitting, the others will be running at low power or off and will not be transmitting. Such a scheme saves power for the portable hand-held gas detector 10 compared to continuous operation of the laser diodes. As mentioned, the main controller 22 is arranged to control the current driver 18 to pulse each laser diode 12*a*-12*d* on via pulsed current drive signals 18*a*-18*d*. Each current drive signal 18*a*-18*d* comprises a combination of a sine wave, triangle (or alternatively sawtooth) wave, and DC offset, each of which may be varied according to the target wavelength of the radiation to be generated by the particular laser diode 12*a*-12*d* being activated. For each current drive signal 18*a*-18*d*, the particular sine and triangle waves are generated by sine wave and triangle wave modules 26 and 28 respectively. In the first preferred form, the sine and triangle wave modules 26, 28 are performed by direct digital synthesis (DDS) chips that are controlled via the serial peripheral interface (SPI) of the main controller 22 and the master clocks of the DDS chips are preferably driven by the pulse width modulation (PWM) output from the main controller 22. The DDS chips can be programmed to generate triangle or sine waves at a particular modulation frequency, which may be the same or alternatively different for each laser diode. The DC offset is provided directly from the main controller 22 via its digital-to-analogue converter (DAC) or PWM output ports. In the first preferred form, the same DDS chips are utilised for generating sine and triangle waves for all the laser diodes.

The sine wave, triangle wave, and DC offset signals are combined in adder 32, such as a 3 signal opamp adder, to generate the particular modulated current drive signal 34 for driving one of the laser diodes 12*a*-12*d* via the output ports 18*a*-18*d* of a demultiplexer 36 that channels the drive signal to the appropriate laser diode 12*a*-12*d* on instruction by the main controller 22. The resistance of the laser diodes 12*a*-12*d* may not be fixed and therefore a voltage-to-current converter, such as a transconductance amplifier, may be utilised on the output of the current driver 18. Further, preferably a zener diode clamp is utilised to limit the output voltage of the adder 32. In the first preferred form, a 3.3 volt zener diode is utilised or alternatively a 3.3 volt roil-to-rail opamp or any other suitable voltage limiting device could be used.

In summary, the main controller 22 controls the current driver 18 to drive the laser diodes 12a-12d in a sequential, predetermined pattern, under the pulsed current driving scheme and co-ordinates the generation of the appropriate current drive signal 18a-18d (combination of sine wave, triangle wave, and DC offset) for each of the laser diodes 12a-12d in turn.

Figure 3:
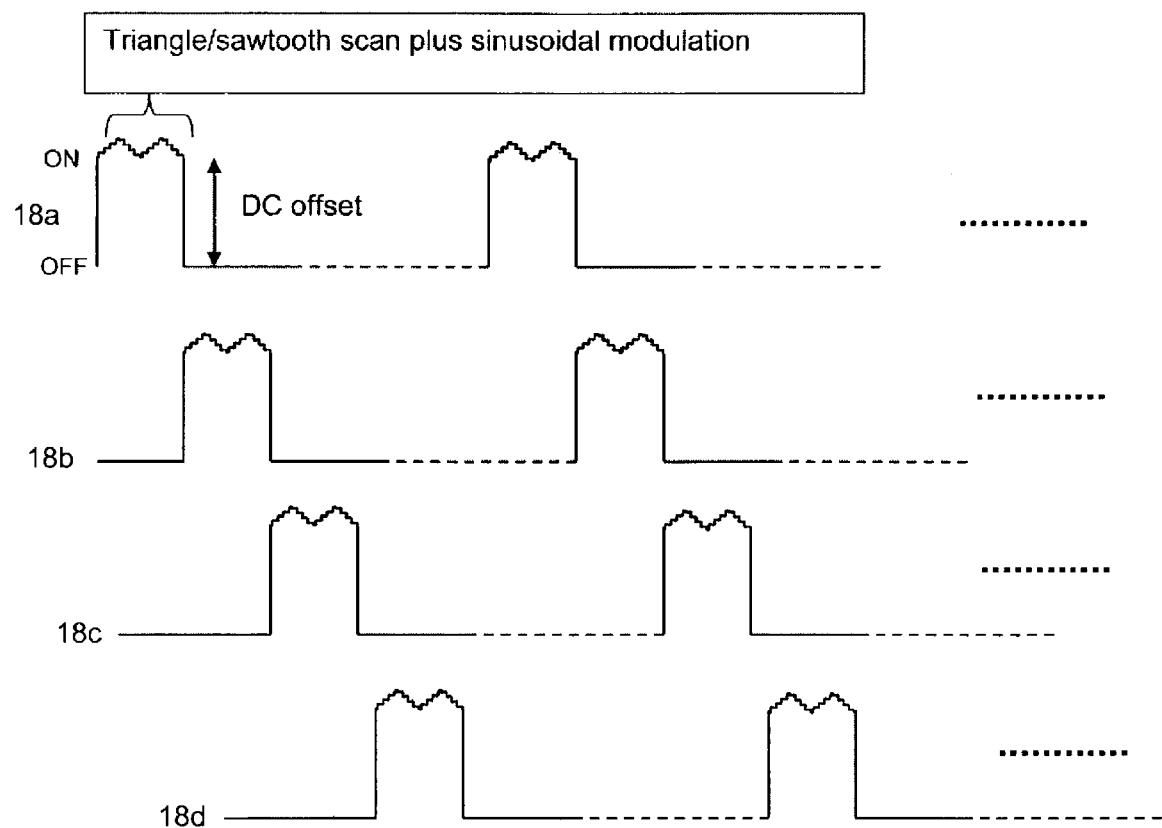
FIG. 3 is a graphical representation of sequential pulsed drive currents generated by the current driver of first preferred form gas detector.

By way of example, FIG. 3 shows an example of the pulsed current driving scheme and a possible predetermined pattern of operation per cycle of current drive signals 18a-18d generated. In summary, during the on period for each laser diode 12a-12d during a cycle, its current drive signal 18a-18d is simultaneously triangularly ramped and sinusoidally modulated in order to produce a scanned, wavelength modulated, infrared radiation output at the laser diode for detecting and measuring the concentration of one of the four target gases at its respective target wavelength. In the first preferred form, the radiation transmitted by the laser diodes is scanned across a small range about each respective target wavelength to allow for long term drifts in each laser's centre wavelength. If no target gas is present, then there is no signal to reference to. The laser's wavelength may drift over time and if a target gas is present it may not be detected due to this drift. Scanning each laser's wavelength over a small range about its center target wavelength helps to ensure that the target wavelength is always present in the laser output and thus minimises the effect of drift. The pulse frequency and pattern, and DC level of the pulsed current driving scheme are preferably set so as to minimise any laser diode temperature variation in the target wavelengths. Further, appropriate setting of the pulse duty cycle and relative phase of the individual pulse drive currents 18a-18d of the laser diodes facilitates reduced power consumption. An additional method for minimising the effects of temperature drift is the implementation of periodic bump testing. The user is requested to expose the detector to a sample of the gases of interest that allows the device to locate the signals and correct for any drift.

Figure 4:
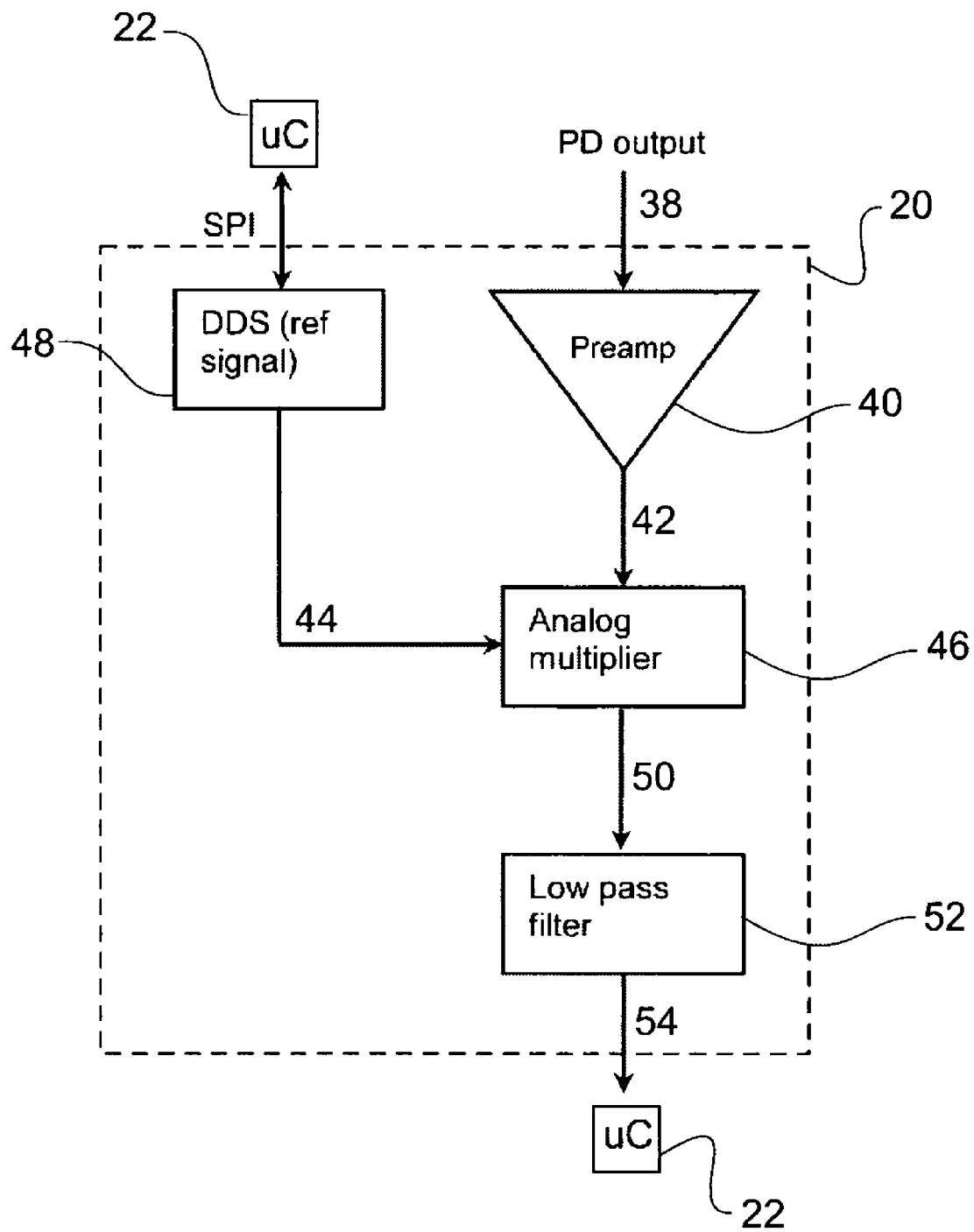
FIG. 4 is a schematic diagram of a lock-in amplifier that amplifies and filters intensity output signals from the optical detector of the first preferred form gas detector.

Referring to FIG. 4, the lock-in amplifier 20 is arranged to amplify and filter the intensity output signal 38 generated by the photodiode 16 in response to detected radiation. Firstly, an amplifying component 40, such as a pre-amp, amplifies the intensity output signal 38. The amplified signal 42 is then multiplied with a reference signal 44 at multiplier 46. The reference signal 44 is generated by a reference signal module 48, such as a DDS chip, that is controlled by the main controller 22 and is phase locked to the laser's sine wave modulation source. As mentioned, the lock-in amplifier 20 is sequentially configured in a synchronous manner according to the activation of the laser diodes 12a-12d such that it obtains the intensity output signal from the photodiode 16 for the target wavelength being transmitted by the currently activated laser diode 12a-12d. In particular, the main controller 22 controls the reference signal module 48 to generate a reference signal 44 associated with the target wavelength of interest, depending on which laser diode 12a-12d is activated. In the first preferred form, the reference signal 44 will be a harmonic of the modulation signal that modulates the radiation transmitted at each target wavelength. By way of example, the modulation signal may be the same for each of the laser diodes. The main controller 22 controls the phase of the reference signal 44 generated by the reference signal module 48. In the first preferred form, the main controller 22 ensures that the phase difference between the reference signal 44 and the modulation frequency component in the photodiode output is zero. Therefore, the main controller 22 controls the phase and frequency of the reference signal 44. In the first preferred form, the lock-in amplifier 20 detection is at twice the modulation frequency and preferably the reference signal 44 from the reference module 48 is filtered, for example, by a band pass filter. The multiplied signal 50 output from the multiplier 46 is then subjected to low pass filter module 52 which extracts the DC component. The final intensity output signal 54 is then processed by the main controller 22 to generate or determine representative concentration level information for the target gas based on a harmonic signal of the radiation at the target wavelength through the gas sample. The main controller may be arranged to process a number of signals and average them before using this average to calculate the gas concentration level for each target gas. This can improve the signal-to-noise ratio.

As mentioned, the laser diodes 12a-12d may, for example, be VCSEL or DFB based lasers, and each emits electromagnetic radiation or waves at one of the specific target wavelengths of the target gases. The wavelength of the radiation emitted by each of the laser diodes 12a-12d is a function of both temperature and driving current. This calls for precision temperature control to an accuracy of approximately 0.1° C. as each of the laser diodes 12a-12d has to be maintained at a different temperature according to its target wavelength. Therefore, there are preferably four independent temperature control modules 24a-24d, one associated with each of the laser diodes 12a-12d. At a general level, each temperature control module 24a-24d comprises a temperature sensor, such as a temperature dependent resistor (thermistor), and a temperature controller or actuator, such as a thermoelectric cooler (TEC). In the first preferred form, the main controller 22 interfaces with the thermistor and TEC of each temperature control module 24a-24d to control the operating temperature of each laser diode 12a-12d depending on the operating parameters required to generate radiation at the respective target wavelengths. The thermistor is connected to a series resistor to act a voltage divider. The thermistor is supplied with a precise bandgap reference voltage generated by the main controller 22. The TEC needs a series resistor to limit current through it.

Figure 5A:
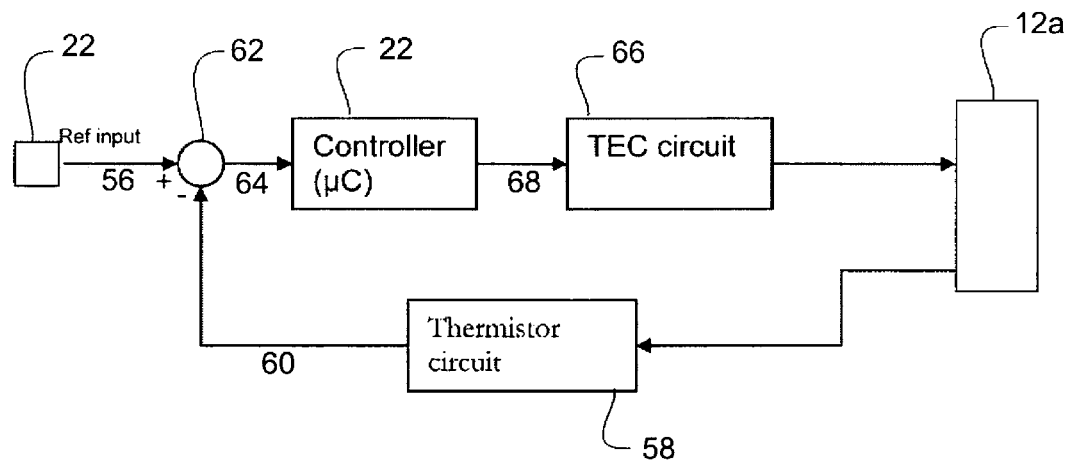
FIG. 5a is a schematic diagram of the closed loop temperature control implemented by temperature control modules of the first preferred form gas detector.

Referring to FIG. 5a, each temperature control module 24a-24d employs closed loop feedback, with the TEC controlling the laser diode temperature according to a desired temperature reference signal and the thermistor sensing and feeding back a signal representing the actual laser diode temperature. By way of example, the temperature control module 24a associated with laser diode 12a will be described, although the general implementation is similar for each of the temperature control modules 24a-24d.

In operation, a desired temperature signal 56 is provided by main controller 22 representing the desired operating temperature of laser diode 12a to generate its target wavelength. The thermistor 58 senses the temperature of the laser diode 12a and generates a representative actual temperature signal 60 which is then compared with the desired temperature signal 56 at error module 62. A series resistor with the thermistor 58 supplied by a regulated voltage may form the temperature-to-voltage converter for the actual temperature signal 60. A temperature difference signal 64 representing the difference between the actual 60 and desired 56 temperature signals is then output from the error module 62 for processing by the main controller 22. The main controller 22 is then arranged to control the TEC 66 via control signals 68 to manipulate the temperature of the laser diode 12a so as to minimise the temperature difference signal 64 and thereby bring the actual temperature closer to the desired temperature. With this closed loop feedback arrangement, the temperature control module 24a maintains the laser diode 12a at the desired operating temperature.

Figure 5B:
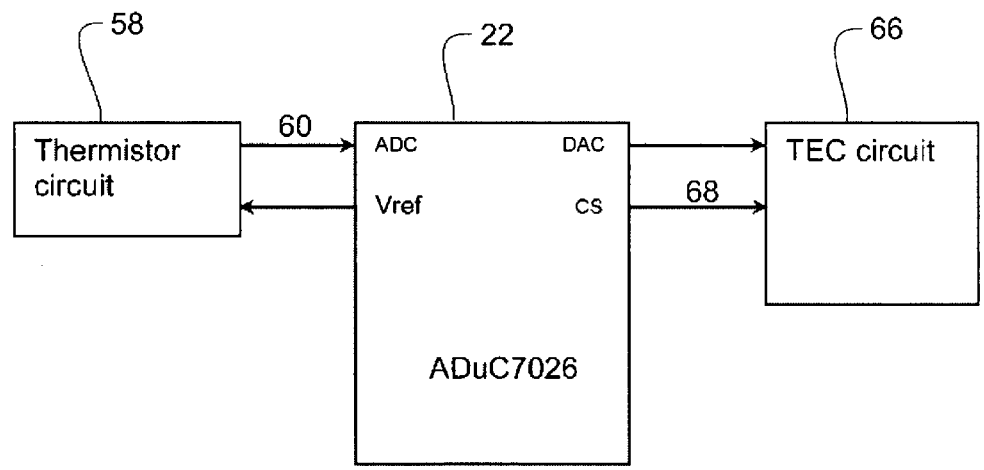
FIG. 5b is a schematic diagram of a temperature control module of the first preferred form gas detector.

FIG. 5b shows one particular arrangement of how the main controller 22 interfaces with the thermistor 58 and TEC 66. In particular, the thermistor 58 provides a representative actual temperature signal 60 to the analogue-to-digital converter (ADC) port of main controller 22. The TEC can heat or cool the laser diode according to the direction of TEC current flow. An H bridge may be utilised for changing the TEC current flow direction. In order to vary the current magnitude, the DAC of the main controller 22 is used to generate the required voltage. This voltage along with the series resistance and TEC resistance generates the required current magnitude. The H-bridge may comprise four analog switches which are controlled by the control signal (CS) from the main controller 22. The temperature control is a software-based discrete proportional-integral-derivative (PID) controller running in the main controller 22.

Second Preferred Form Gas Detector

Figure 6:
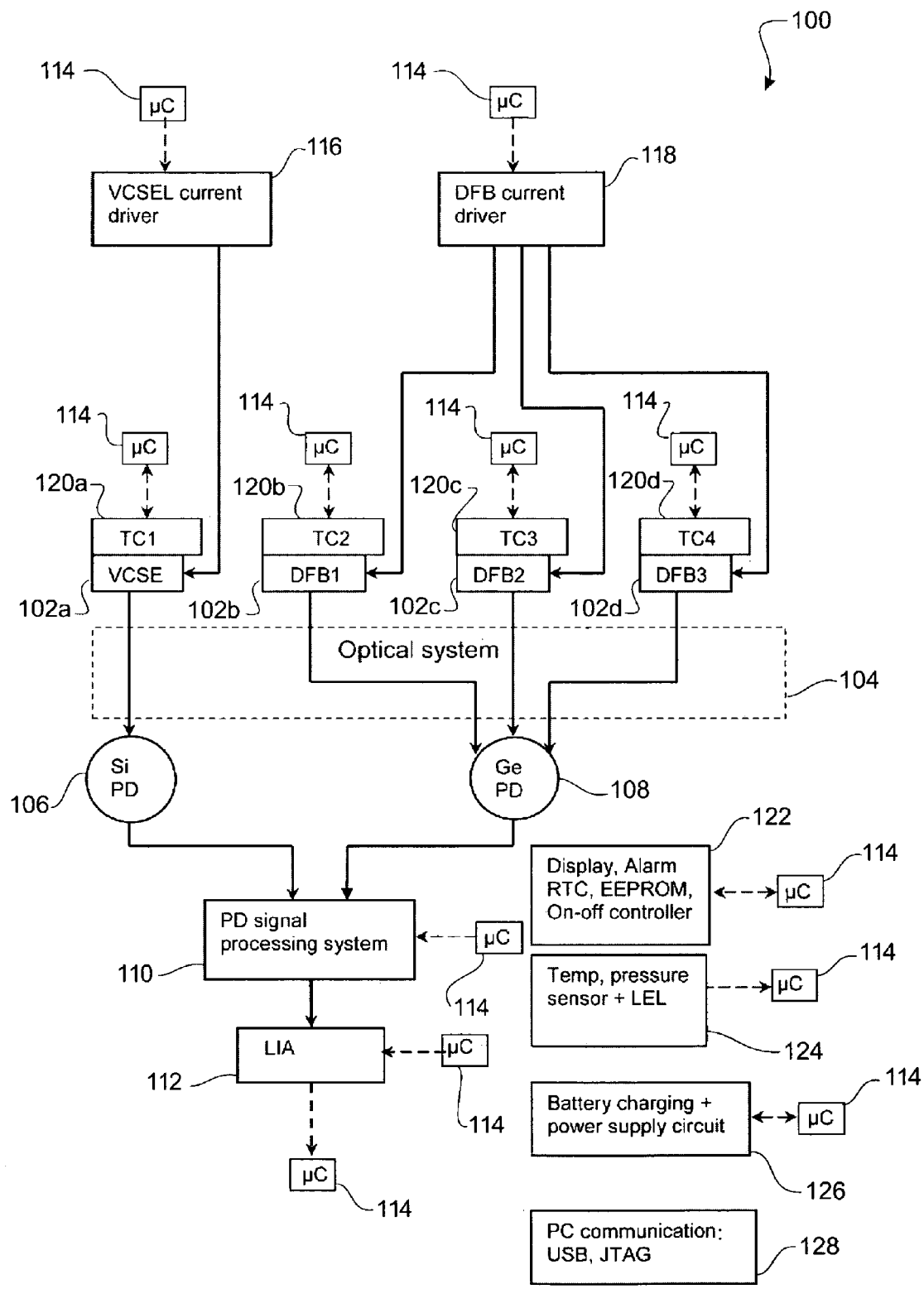
FIG. 6 is a schematic diagram of a second preferred form gas detector of the invention.

Referring to FIG. 6, a schematic diagram of a second preferred form gas detector 100 is shown. The second preferred form gas detector 100 is similar in functionality to that of the first preferred form gas detector 10 although there are differences in configuration that will be explained.

The gas detector 100 is arranged to sense the concentration levels of the same four target gases, namely oxygen, carbon monoxide, methane and hydrogen sulphide. Like gas detector 10, four laser sources 102a-102d are provided for transmitting infrared radiation at four target wavelengths corresponding to the optimum absorption wavelengths of the four target gases. The radiation is transmitted through a gas space 104 that contains a gas sample from the environment surrounding the gas detector 100. In the second preferred form, a VCSEL laser 102a is utilised for detecting the oxygen concentration level and three DFB lasers 102b-102d are utilised for detecting the concentration levels of carbon monoxide, methane and hydrogen sulphide respectively. The radiation transmitted by VCSEL laser 102a through the gas sample is sensed by optical detector 106. The radiation transmitted by the three DFB lasers 102b-102d through the gas space 104 is sensed by optical detector 108. The output signals from the optical detectors 106,108 are processed by optical detector signal processing module or system 110 before being amplified and filtered by lock-in amplifier 112. In the second preferred form, the optical detectors 106,108 are photodiodes and the signal processing module is referred to as a photodiode signal processing module 110. By way of example, the optical detector 106 may be a silicon (Si) photodiode and the optical detector 108 may be a germanium (Ge) photodiode.

The output signals from the lock-in amplifier 112 are then processed by the main controller 114 to generate representative gas concentration levels based on the radiation absorption levels at the target wavelength in a manner previously described with respect to the first preferred form gas detector 10.

The gas detector 100 comprises a first current driver 116 for driving the VCSEL laser 102a and a second current driver 118 is arranged to drive the three DFB lasers 102b-102d. The first current driver 116 preferably activates the VCSEL 102a continuously. The second current driver 118 is arranged to sequentially activate the three DFB lasers 102b-102d one at a time in a cycle using pulsed drive currents. Therefore, at any one time only one of the three DFB laser diodes 102b-102d will be activated to transmit radiation while the VSCEL laser diode 102a is preferably activated continuously. It will be appreciated that the VSCEL laser diode 102a could alternatively be activated in a pulsed manner to save power if desired.

The gas detector 100 also includes the same main other subsystems described in respect of the first preferred form gas detector 10. In particular, the gas detector 100 comprises four individual temperature control modules 120a-120d for actively controlling the operating temperature of the laser diodes 102a-102d. The gas detector 100 also comprises an output display, alarm modules, memory (such as EEPROM or the like), on/off controller, real-time clock (RTC), output ports (USB, JTAG, or the like) for transferring data to computers or other devices, temperature sensor, pressure sensor, LEL, and power supply circuitry and charging circuitry as shown in modules 122,124,126 and 128.

Figure 7:
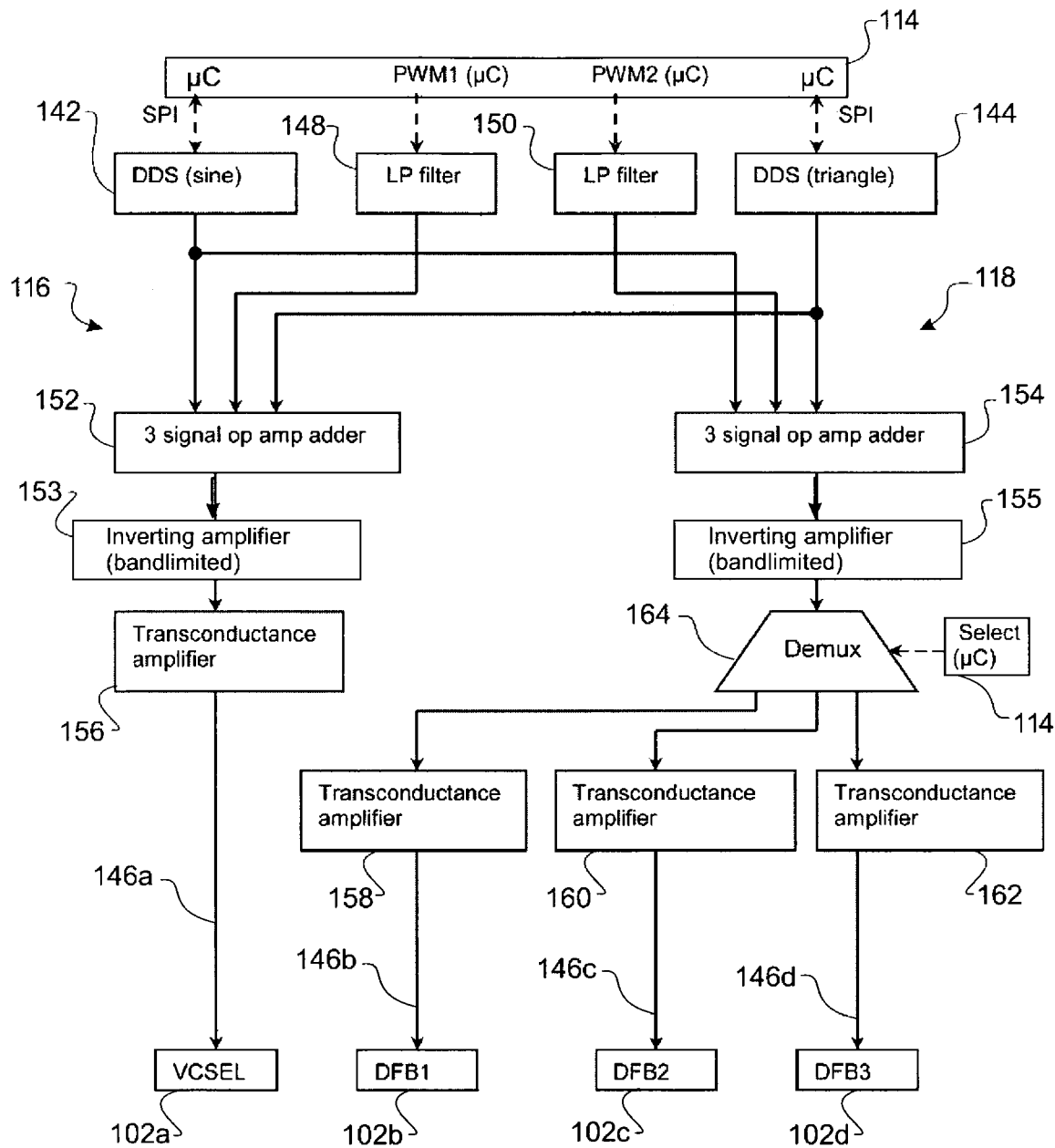
FIG. 7 is a schematic diagram of the current drivers for the laser sources of the second preferred form gas detector.

Referring to FIG. 7, a schematic diagram of the first 116 and second 118 current drivers for the laser diodes 102a-102d is shown. In the second preferred form, the first current driver 116 is arranged to continuously activate VCSEL laser 102a while the second current driver 118 is arranged to sequentially activate the three DFB lasers 102b-102d one at a time in a predetermined pattern or order and in a repeating cycle using pulsed drive currents. As previously described with respect to the first preferred form gas detector 10, the drive currents for the laser diodes 102a-102d comprise a sine wave, triangle wave, and DC offset to cause the laser diodes to transmit radiation, at each of the target wavelengths, that is sinusoidally modulated at the sine wave frequency and ramped according to the triangle wave. The current drive signals are modulated so that small signals can be extracted from the background noise using the lock-in amplifier 112 as will be described later.

DDS modules 142 and 144 generate the sine waves and triangle waves for the current drive signals 146a-146d. DDS modules 142,144 are controlled by the main controller 114 and preferably each of the current drive signals 146a-146d for the laser diodes 102a-102d comprise the same sine wave and triangle wave modulation frequencies or components. The VSCEL and DFB lasers utilise different DC offsets and therefore the main controller outputs two different DC inputs. In particular, the DC offset for the VCSEL laser 102a is provided by the main controller 114 via a low pass filter 148 while the DC offset signal for the three DFB lasers 102b-102d is provided by the main controller 114 via low pass filter 150. Further, the DC offsets for each of the DFB lasers 102b-102d will likely be different as each laser will have its own requirement for the DC offset to give the target wavelength required.

As the current drive signal level (sine wave, triangle wave and DC magnitude) is different for the DFB and VSCEL lasers, the first and second current drivers 116 and 118 comprise separate adders 152 and 154 respectively, such as three-signal opamp adders, for adding the sine wave, triangle wave and DC offset signals. The output of the adders 152 and 154 are voltage drive signals and are passed through bandlimited inverting amplifiers 153,155 respectively. Then the signals are converted to current drive signals via transconductance amplifiers 156,158,160,162 as the resistance of the laser diodes 102a-102d is not fixed. The pulsed driving scheme for sequentially activating DFB lasers 102b-102d is controlled by the main controller 114 via the demultiplexer 164 in a manner similar to that described in respect of the first preferred form gas detector 10.

Figure 8:
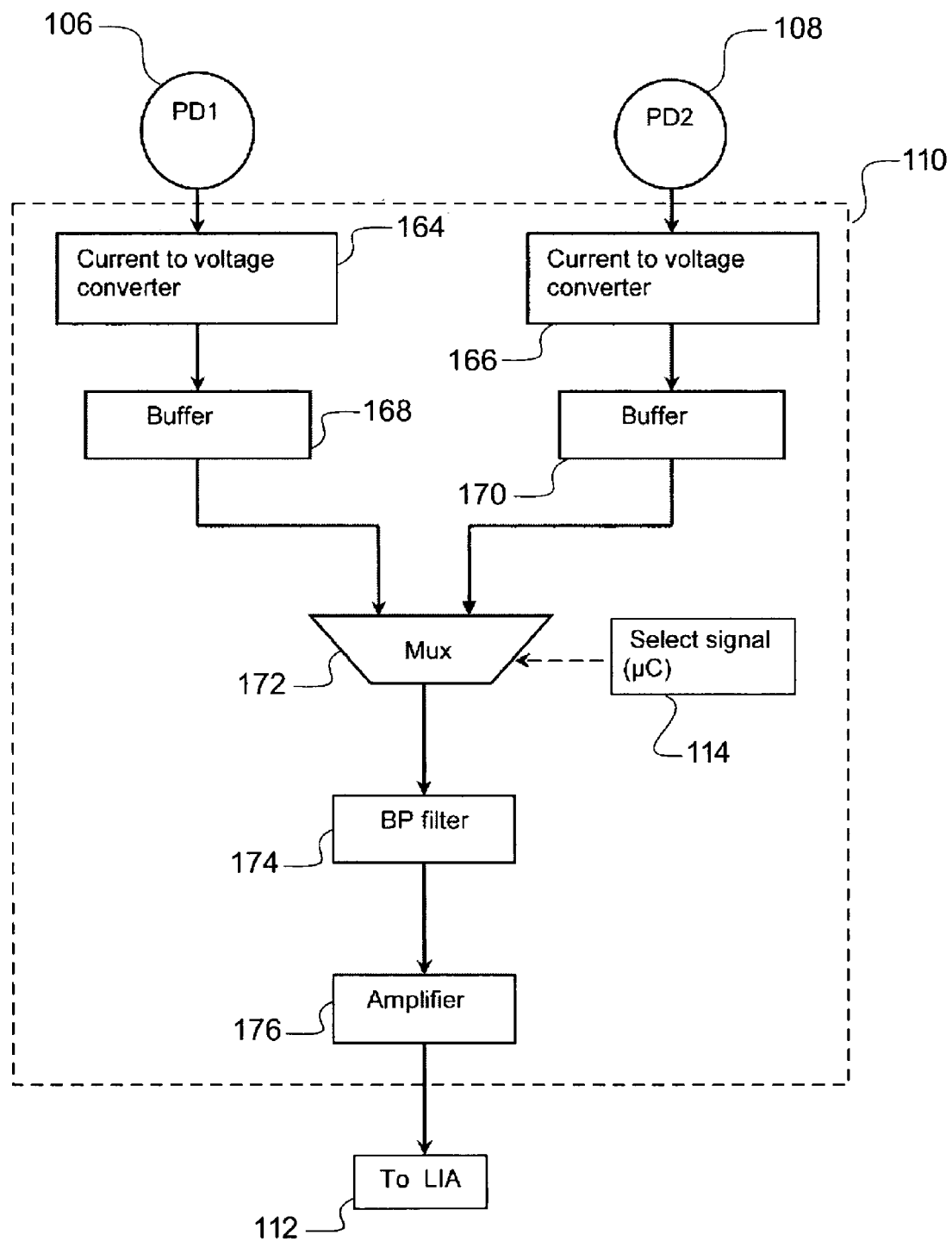
FIG. 8 is a schematic diagram of the signal processing modules for the optical detectors of the second preferred form gas detector.

Referring to FIG. 8, the signal processing modules or system 110 for processing the output signals from the optical detectors 106 and 108 is shown. In the second preferred form, the optical detector 106 for the VSCEL laser 102a is preferably a silicon (Si) photodiode. The optical detector 108 for the DFB laser diodes 102b-102d is preferably a Germanium (Ge) or Indium Gallium Arsenide (InGaAs) photodiode. The output signals from the photodiodes 106,108 generated in response to the sensed radiation transmitted through the gas sample are passed through current-to-voltage converters 164, 166 and buffers 168 and 170. The main controller 114 of the control system is arranged to then selectively channel the buffered signals from the optical detectors 106,108 to the lock-in amplifier 114 via multiplexer 172 so that the concentration levels for the target gases can be determined one at a time in a predetermined pattern in a repeating cycle substantially similar to that described with respect to the first preferred form gas detector 10. Further processing of the signals is provided after the multiplexer 172. In particular, the multiplexed signal is band pass filtered 174 to remove unwanted frequency components and then amplified 176 before being mixed in the lock-in amplifier 112.

Figure 9:
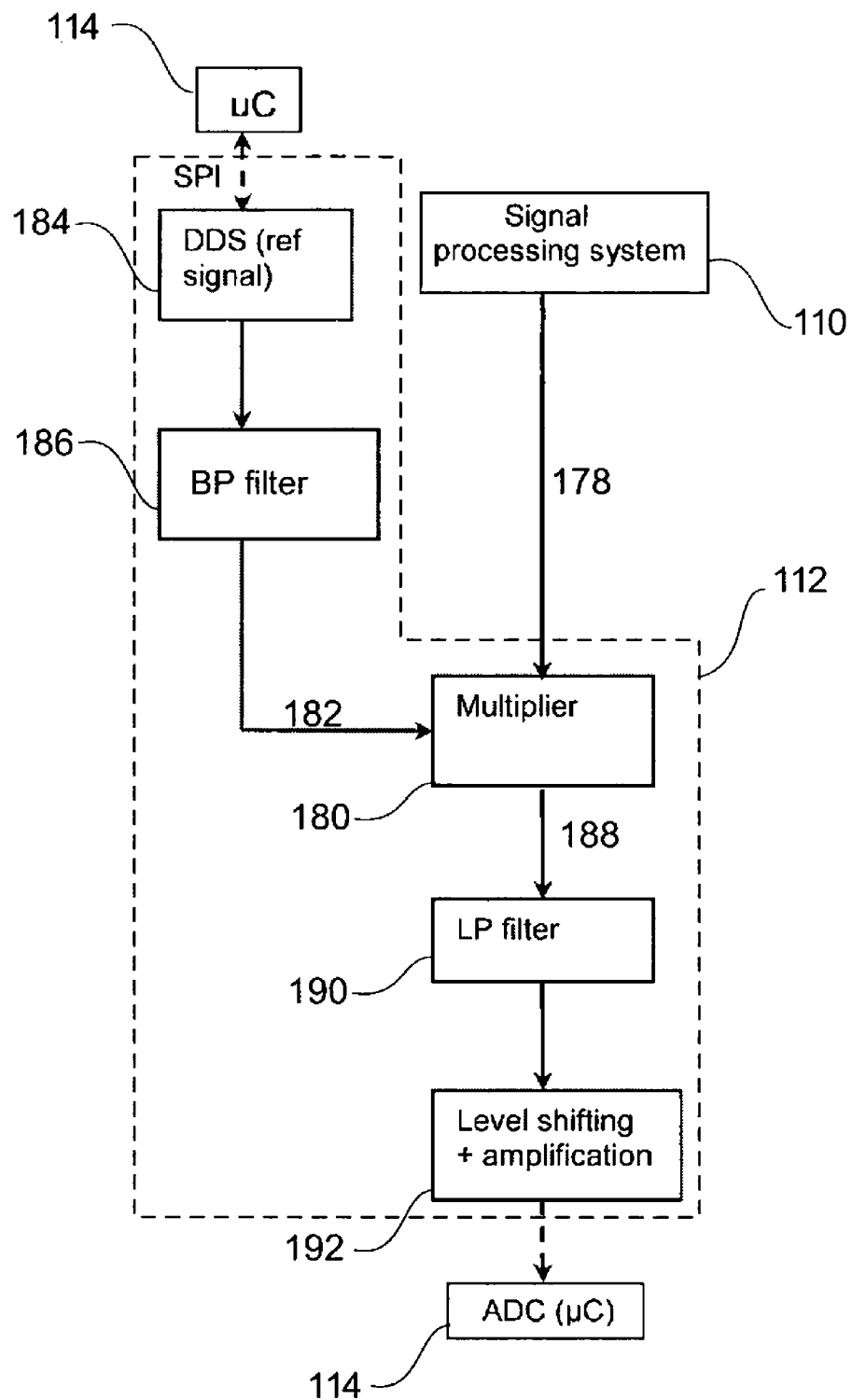
FIG. 9 is a schematic diagram of a lock-in amplifier that amplifies and filters intensity output signals from the signal processing modules of the second preferred form gas detector.

Referring to FIG. 9, a schematic diagram of the lock-in amplifier 112 of the gas detector 100 is shown. The lock-in amplifier 112 is arranged to filter the signal from the photodiode signal processing system 110. In particular, the lock-in amplifier 112 is arranged to extract a harmonic of the radiation modulation frequency from the photodiode signal for processing to determine the gas concentration levels for the target gases. The output signal 178 from the photodiode signal processing system 110 is input into the multiplier (mixer) 180 of the lock-in amplifier 112. The multiplier 180 is preferably a four quadrant analogue multiplier that mixes the output signal 178 with a phase locked sinusoidal reference signal 182 generated by a DDS chip 184 as controlled by the main controller 114. The reference signal 182 is passed through a bandpass filter and amplifier 186. The frequency of the reference signal 182 as generated by the DDS chip 184 is the frequency component that is to be extracted from the photodiode output signal, and preferably is a harmonic of the modulation frequency. In one form, the reference signal 182 may have a frequency that is twice (or some other integer multiple) of the modulation frequency of the sine wave generated within the current drivers 116,118. The mixed signal 188 is then passed through a low pass filter 190 and a level-shifting and amplification module 192 before being processed by main controller 114 to determine the gas concentration level.

Figure 10:
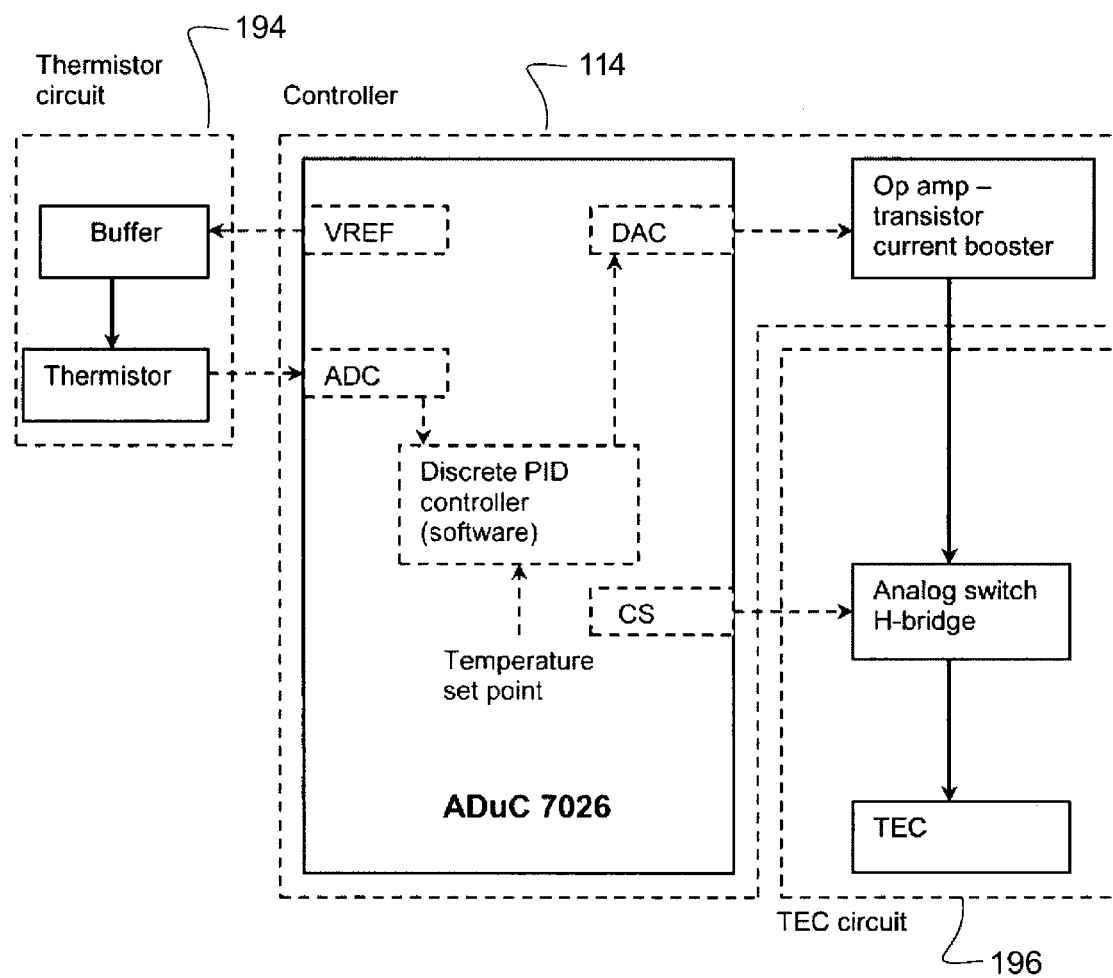
FIG. 10 is a schematic diagram of a temperature control module of the second preferred form gas detector.

Referring to FIG. 10, a schematic of one of the temperature control modules 120a-120d of the gas detector 100 is shown along with the micro-controller. The temperature control modules 120a-120d operate in the same way as those described with respect to FIGS. 5a and 5b of the first preferred form gas detector 10. In particular, the main controller 114 implements a discrete PID controller (software) to control the operating temperature of each of the laser diodes 102a-102d in accordance with preset temperature set points with closed loop feedback. The discrete PID controller interfaces with thermistor circuits 194 for sensing the actual temperatures of the laser diodes 120a and a TEC circuit 196 for actively controlling the temperatures of the laser diodes in accordance with the desired set points.

Figure 11:
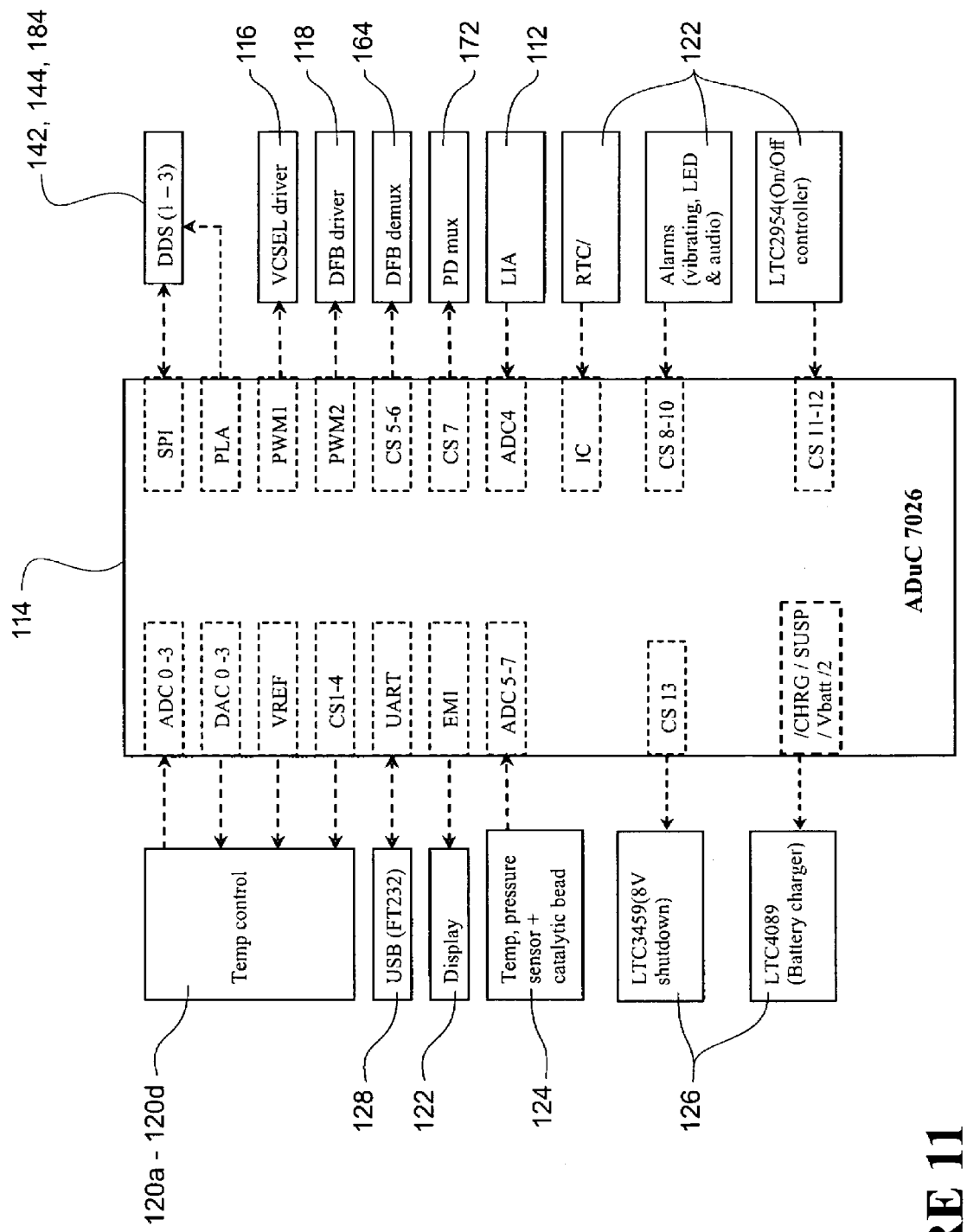
FIG. 11 is a schematic diagram of the main controller of the second preferred form gas detector interfacing with main subsystems of the detector.

FIG. 11 shows a possible configuration of the main controller 114 interfacing with the other main subsystems.

Third Preferred Form Gas Detector

Figure 12:
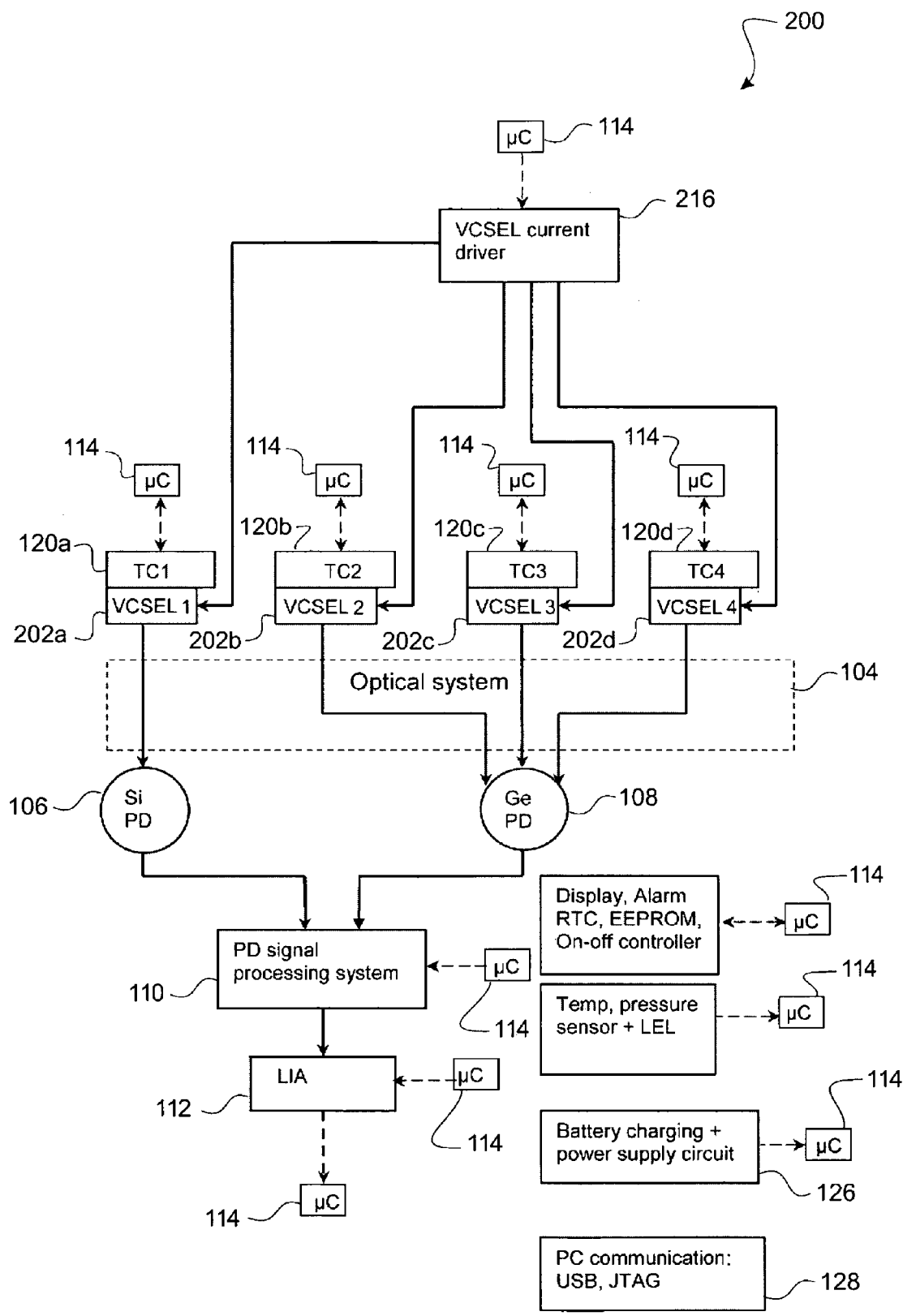
FIG. 12 is a schematic diagram of a third preferred form gas detector of the invention.

Referring to FIG. 12, a schematic diagram of a third preferred form gas detector 200 is shown. The third preferred form gas detector 200 is similar in functionality and configuration to that of the second preferred form gas detector 100 with like components being referenced by like reference numbers. The primary difference between the gas detectors 100 and 200 is that gas detector 200 utilises four VCSEL laser diodes 202a-202d for the laser sources for detecting oxygen, carbon monoxide, methane and hydrogen sulphide. The advantage of using VCSEL laser diodes over DFB laser diodes is that the operating power requirements of VCSEL laser diodes are less than DFB laser diodes and therefore provide power savings.

Figure 13:
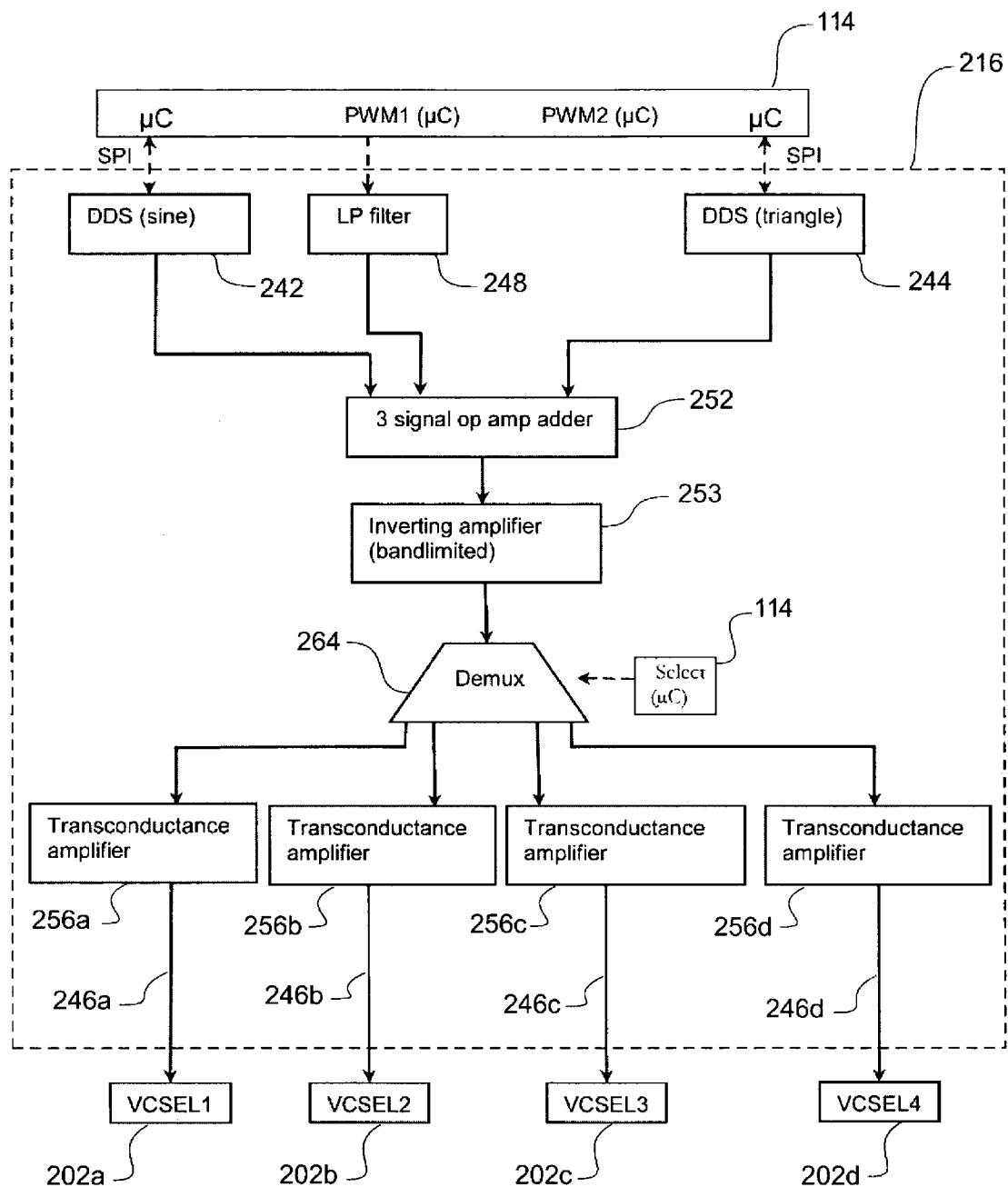
FIG. 13 is a schematic diagram of the current driver for the laser sources of the third preferred form gas detector.

The VCSEL laser diodes 202a-202d are driven by a single current driver 216 which will now be described with reference to FIG. 13. The current driver 216 is arranged to generate the current drive signals 246a-246d for the laser diodes 202a-202d. The current driver 216 is similar to the configuration of the first current driver 116 of the second preferred form gas detector 100. DDS modules 242,244 generate the sine and triangle waves respectively for the current drive signals 246a-246d. DDS modules 242,244 are controlled by the main controller 114 and preferably the current driver signals 246a-246d comprise the same sine wave and triangle wave modulation frequencies or components. The DC offset for the current drive signals 246a-246d is provided by the main controller 114 via a low pass filter 248. The sine wave, triangle wave and DC offset signals are added together by adder 252, which may for example be a 3-signal op amp adder or the like. The output of the adder 252 is a voltage drive signal that is passed through a bandlimited inverting amplifier 253. Following the inverting amplifier 253 is a demultiplexer 264 which is controlled by the main controller 114 to selectively channel the output signal from the inverting amplifier 253 to one of the VCSEL laser diodes 202a-202d in a predetermined order or pattern that repeats in a manner similar to that described in respect of the first 10 and second 100 preferred forms of the gas detector. The four outputs of the demultiplexer 264 are connected to the inputs of the VCSEL laser diodes 202a-202d via respective transconductance amplifiers 256a-256d that are arranged to convert the voltage drive signals from the demultiplexer 264 into current drive signals 246a-246d.

Optical System Configurations

In the preferred forms 10,100,200 of the gas detector described above, the gas space 14,104 of the gas detector may preferably but not necessarily contain an optical system that is arranged to provide modified radiation transmission paths (and therefore modified path lengths) in the gas space for one or more of the laser sources according to the sensitivity required for each particular target gas. The radiation emitted at the target wavelengths for detecting oxygen and methane may be transmitted along a shorter direct straight path through the gas sample. In contrast, the radiation emitted at the target wavelengths for detecting carbon monoxide and hydrogen sulphide is preferably transmitted along a longer transmission path, for example a zigzagged path through the gas sample. Generally, the longer transmission paths allow gases having smaller concentrations to be detected. Oxygen, in a habitable environment, generally has high concentration levels and therefore a direct shorter transmission path can be utilised. Methane has optical absorption properties at its optimum target wavelength that allow for a shorter direct transmission path to be utilised also.

By way of example, Table 2 below summarises the preferred radiation transmission path length ranges and optimal path lengths for each laser source and its associated target gas.

TABLE 2

| Laser Source | Target Gas | Preferred Radiation Transmission Path Length Range, and Optimum Path Length |
|---|---|---|
| 12a, 102a, 202a | Oxygen | 0.01 m-0.1 m, preferably 0.05 m |
| 12b, 102b, 202b | Carbon Monoxide | 20 m-50 m, preferably 30 m |
| 12c, 102c, 202c | Methane | 0.05 m-0.2 m, preferably 0.1 m |

TABLE 2-continued

| Laser Source | Target Gas | Preferred Radiation Transmission Path Length Range, and Optimum Path Length |
|---|---|---|
| 12d, 102d, 202d | Hydrogen Sulphide | 10 m-35 m, preferably 20 m |

In the preferred form, the optical system may comprise a multi-pass cell for modifying and increasing the radiation transmission path lengths through the gas sample for the laser sources detecting carbon monoxide and hydrogen sulphide relative to a direct path through the gas space. The multi-pass cell may comprise two opposed reflecting surfaces, such as mirrors, located in the gas space and which are arranged to reflect the infrared radiation transmitted from the laser sources multiple times back and forth within the gas space before exiting the gas space for detection. Various shapes of mirrors can be utilised, including planar mirrors and curved mirrors, such as spherical concave mirrors and cylindrical concave mirrors. Various examples of multi-pass cells for the optical system of the gas detector will be described below.

Example 1

Planar Mirror Multi-Pass Cell

Figure 14:
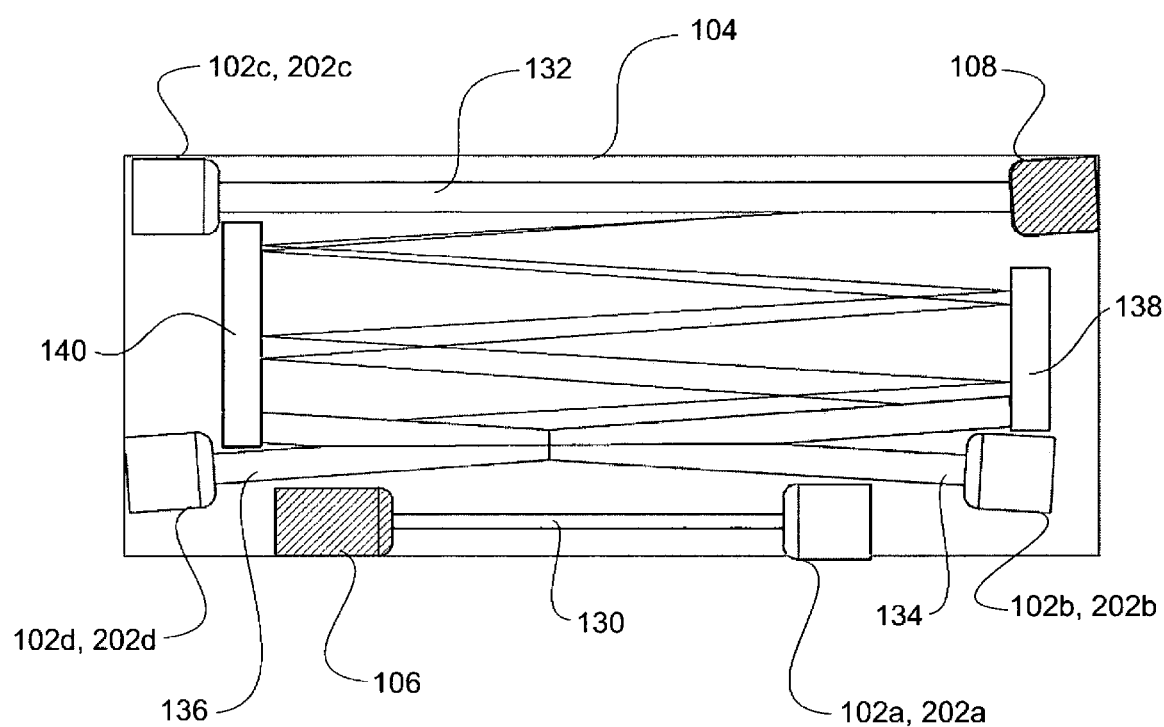
FIG. 14 is a schematic diagram of an arrangement of laser sources and optical detectors for the second or third preferred forms of the gas detector, including an optical system having a multi-pass cell with planar mirrors.

Referring to FIG. 14, an example of a multi-pass cell having a pair of opposed planar mirrors for increasing the path length of infrared radiation emitted from the laser sources that are detecting carbon monoxide and hydrogen sulphide is shown. The planar mirror multi-pass cell example will be described with reference to the second 100 and third 200 preferred forms of the gas detector where like numbers reference like components.

Laser diode 102a, 202a is arranged to transmit radiation 130 through the gas space 104 directly to photodiode 106 for sensing the oxygen concentration level. Likewise, laser diode 102c,202c is arranged to transmit radiation 132 directly through the gas space 104 to photodiode 108 for detecting the methane concentration level. In contrast, laser diodes 102b, 202b and 102d,202d for detecting carbon monoxide and hydrogen sulphide concentrations levels respectively are arranged to transmit respective radiation 134 and 136 in a zigzagged path through the gas space 104 via the optical system for detection by photodiode 108. The optical system comprises a multi-pass cell having a pair of parallel opposed planar reflecting surfaces 138 and 140, such as planar mirrors. Therefore, the radiation transmission paths for detecting oxygen and methane are shorter direct straight paths and the radiation transmission paths for detecting carbon monoxide and hydrogen sulphide are longer zigzagged paths. As mentioned, manipulating the radiation transmission paths and path lengths through the gas sample enables the sensitivity to be altered for each of the target gases depending on requirements.

Typically, the path length for each target gas is determined based on the chosen target wavelength for the target gas (as this determines the gas absorption parameters), the required detection limit, and the system noise. Oxygen has a high concentration level in the atmosphere and therefore a shorter path length can be utilised. Methane has a stronger maximum absorption (line strength) relative to carbon monoxide and hydrogen sulphide and therefore can utilise a shorter path length also. The longer zigzagged transmission paths of radiation 134 and 136 for carbon monoxide and hydrogen sulphide are required to enhance sensitivity for detecting the small concentration levels likely in the gas sample and given the optical absorption characteristics of these gases.

Example 2

Spherical Concave Mirror Multi-Pass Cell with Single Aperture

Figure 15:
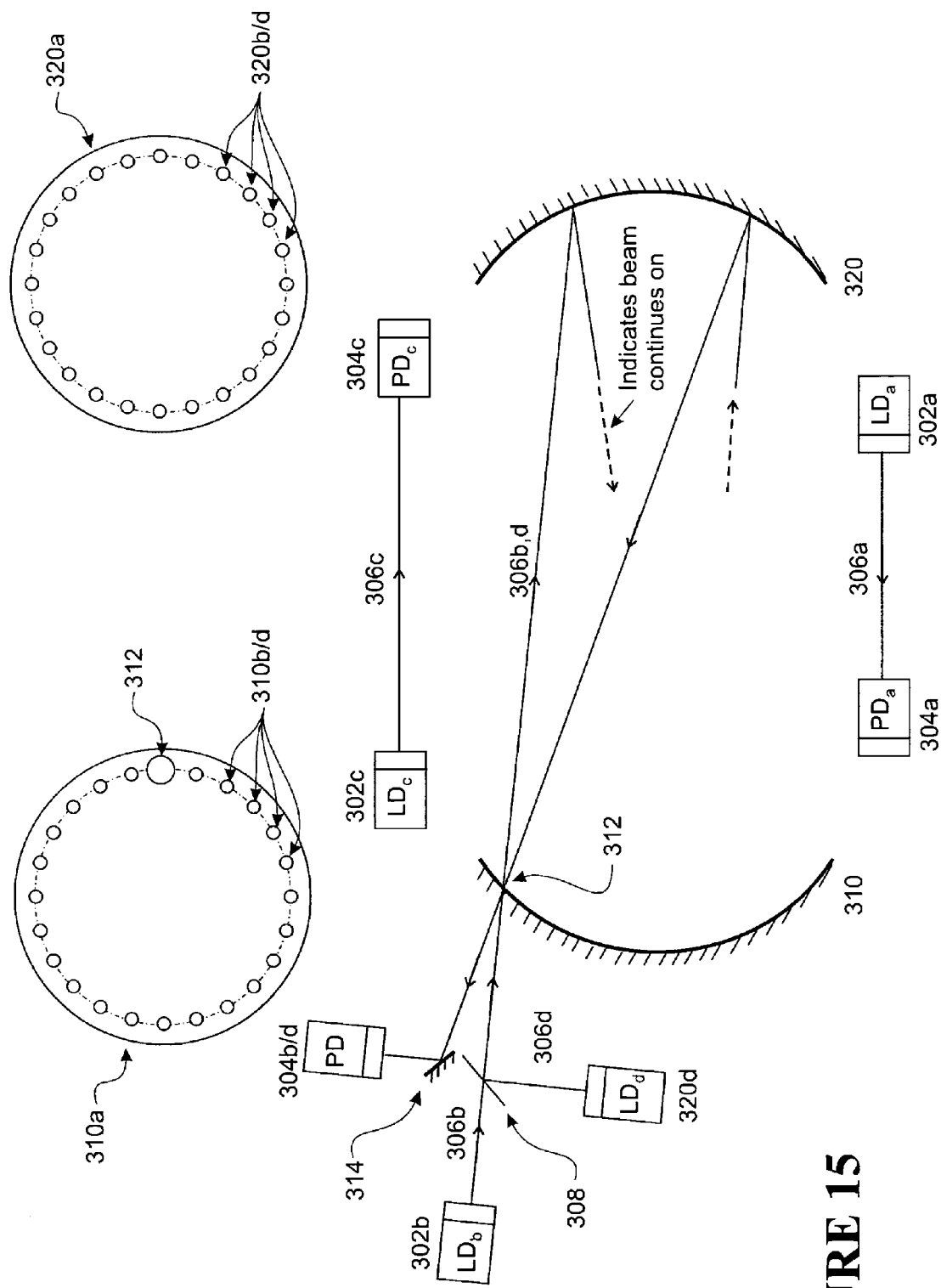
FIG. 15 is a schematic diagram of an arrangement of laser sources and optical detectors for another possible form of the gas detector, including an optical system haying a multi-pass cell with spherical concave mirrors and a single input/output aperture.

With reference to FIG. 15, an arrangement of laser sources 302a-302d (for example laser diodes such as VCSEL lasers or DFB lasers) and optical detectors 304a,304c,304b/d (for example photodiodes) is shown. Laser sources 302a,302c transmit infrared radiation 306a,306c directly to their respective optical detectors 304a,304c for detecting oxygen and methane respectively. Laser sources 302b,302d transmit infrared radiation beams 306b,306d via beam splitter 308 and into an optical system. The optical system comprises a multi-pass cell having a pair of opposed spherical reflecting surfaces, such as spherical concave mirrors 310,320, which are arranged to fold the infrared radiation 306b,306d back and forth between the mirrors multiple times to increase the beam path length through the gas sample between the mirrors. The multi-pass cell is in the form of a Herriot cell.

Infrared radiation 306b,306d is transmitted via the beam splitter 308 through a single input/output aperture 312 located toward the periphery of the first spherical mirror 310 and then onto the reflecting surface of the second spherical mirror 320. The infrared radiation then bounces back and forth between the two mirrors 310,320 until the radiation beams exit the multi-pass cell through the input/output aperture 312. The exiting beams 306b,d are reflected by a planar mirror 314 toward the optical detector 304b/d.

Schematic diagrams 310a and 320a show a front view of the reflecting surfaces of the first 310 and second 320 mirrors with the input/output aperture 312 being shown. The laser spots 310b/d and 320b/d spaced about the periphery of the reflecting surfaces are examples of the reflection points on the surfaces after the infrared radiation has entered the multi-pass cell through the aperture 312 and is periodically reflected and refocused by the mirrors 310,320 before exiting the multi-pass cell through the input/output aperture 312. It will be appreciated that an alternative form of the multi-pass cell may comprise separate input and output apertures in the same or opposite mirrors though which the infrared radiation from the laser sources 302b,302d may enter and exit the cell. The laser spot patterns 310b/d,320b/d on the reflecting surfaces of the mirrors 310a,320a will be in the form of an ellipse. The total path length created by the multi-pass cell can be approximated by the number of passes back and forth between the mirrors 310,320 multiplied by the distance or separation between the mirrors. The maximum number of passes depends on the mirror diameter and the input/output aperture diameter.

Example 3

Spherical Concave Mirror Multi-Pass Cell with Two Apertures

Figure 16:
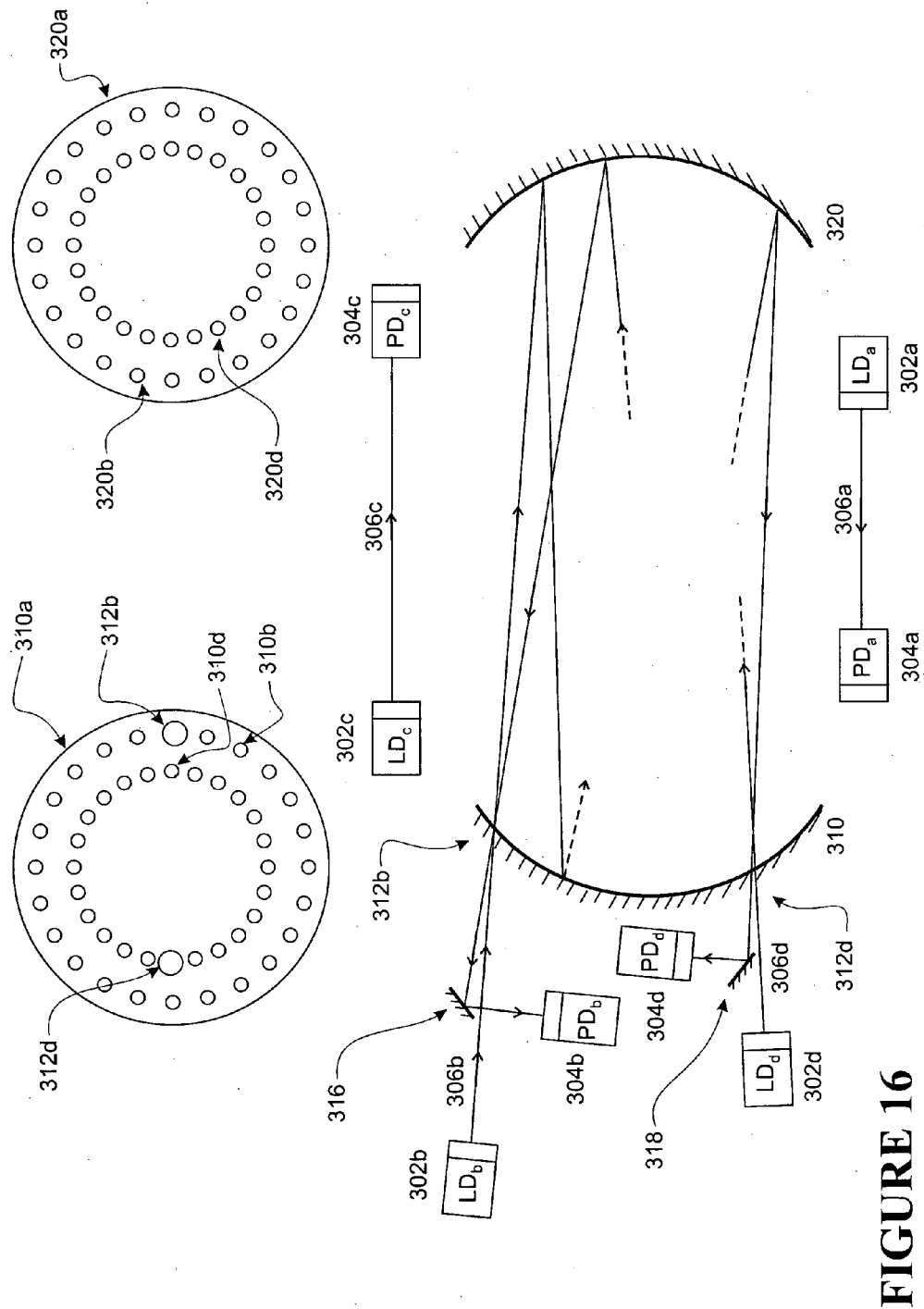
FIG. 16 is a schematic diagram of an arrangement of laser sources and optical detectors for another possible form of the gas detector, including an optical system having a multi-pass cell with spherical concave mirrors and two input/output apertures.

With reference to FIG. 16, a modification to the arrangement of example 2 will be described. Like numbers represent like components. In the modified arrangement shown in FIG. 16, the first spherical concave mirror 310 is provided with two input/output apertures 312b and 312d through which respective infrared beams 306b and 306d from respective laser sources 302b and 302d may enter and exit the multi-pass cell. Schematic diagrams 310a and 320a show the modified laser spot patterns on the reflecting surfaces of the mirrors 310 and 320. As shown, the input/output aperture 312b for the carbon monoxide laser beam 306b is located further toward the periphery of the first mirror 310 relative to the input/output aperture 312d for the hydrogen sulphide laser beam 306d. This results in outer elliptical laser spot patterns 310b,320b for the carbon monoxide detecting laser beam and inner elliptical laser spot patterns 310d,320d for the hydrogen sulphide detecting laser beam on the reflecting surfaces 310a and 320a. Upon exiting the multi-pass cell via the input/output apertures 312b,312d the laser beams 306b,306d are reflected by respective planar mirrors 316,318 to respective optical detectors 304b,304d.

It will be appreciated that the multi-pass cell may have multiple input/output apertures or alternatively separate input and output apertures on the same or opposite mirrors in alternative forms if desired. It will also be appreciated that all of the laser beams 306a-306d may be arranged to enter and exit the multi-pass cell to modify and increase their radiation transmission path lengths through the gas sample relative to a direct transmission path through the gas sample. In the example above, two laser beams 306b,306d propagate within the multi-pass cell in a non-interfering manner in separate regions of the reflecting surfaces 310a,320a and this arrangement can be extrapolated to three or four of the laser beams if desired.

Example 4

Cylindrical Concave Mirror Multi-Pass Cell

Figure 17A:
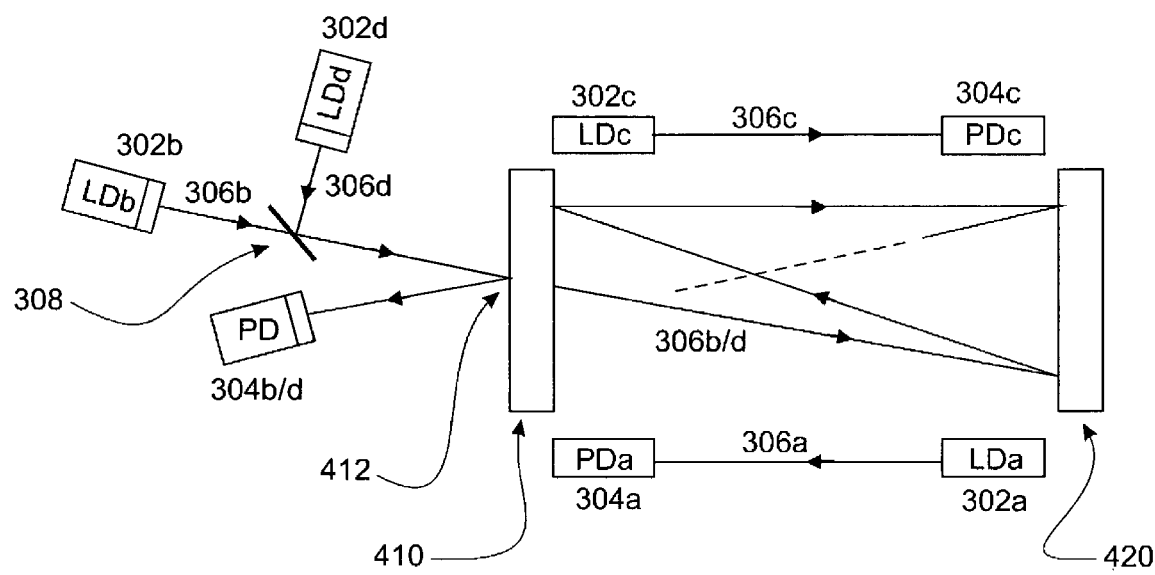
FIG. 17a is a schematic diagram of an arrangement of laser sources and optical detectors for another possible form of the gas detector, including an optical system having a multi-pass cell with cylindrical concave mirrors.
Figure 17B:
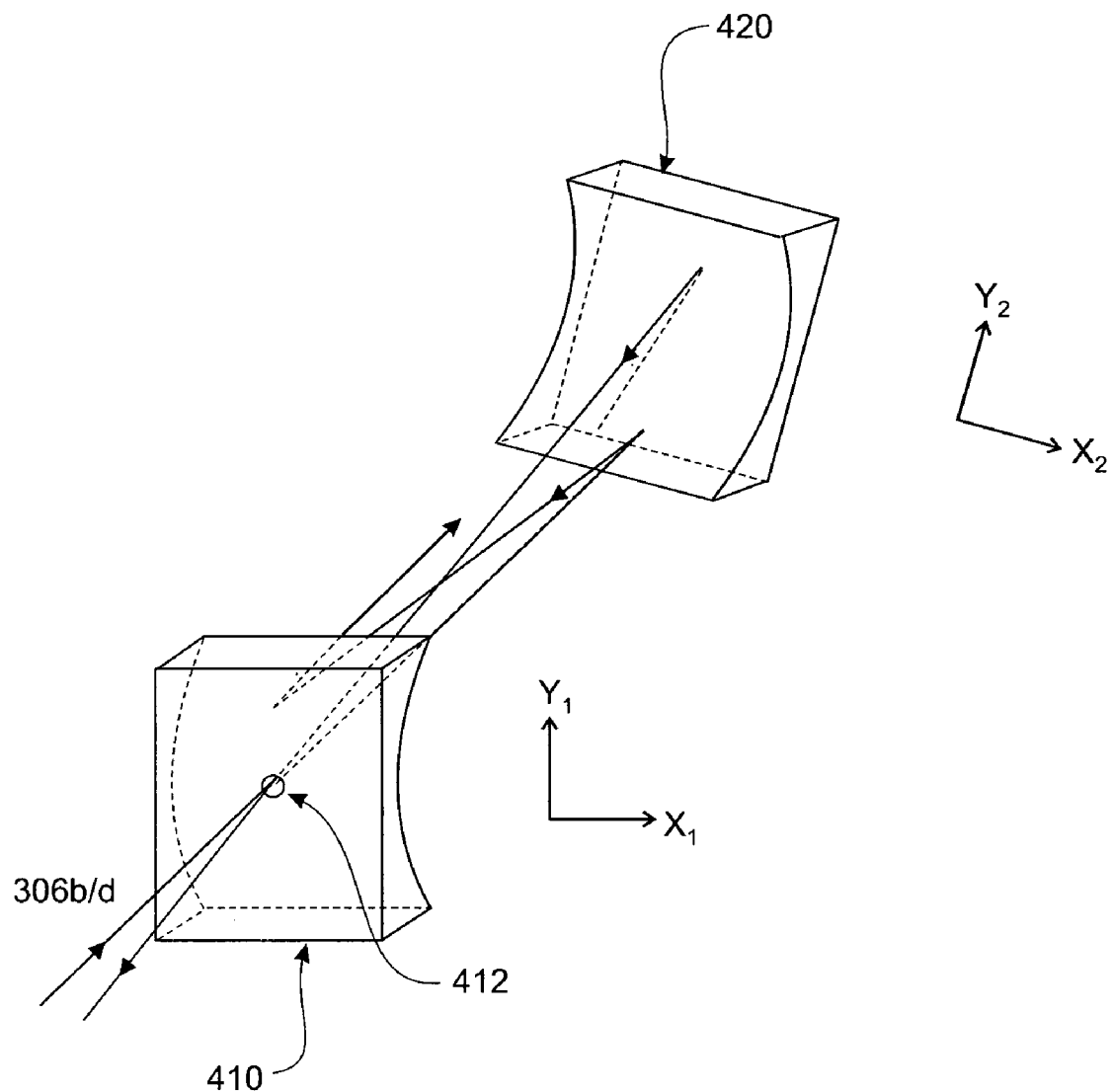
FIG. 17b is the perspective view of the cylindrical concave mirrors of the optical system shown in FIG. 17a and in particular showing the reflection of laser light between the cylindrical concave mirrors.
Figure 17C:
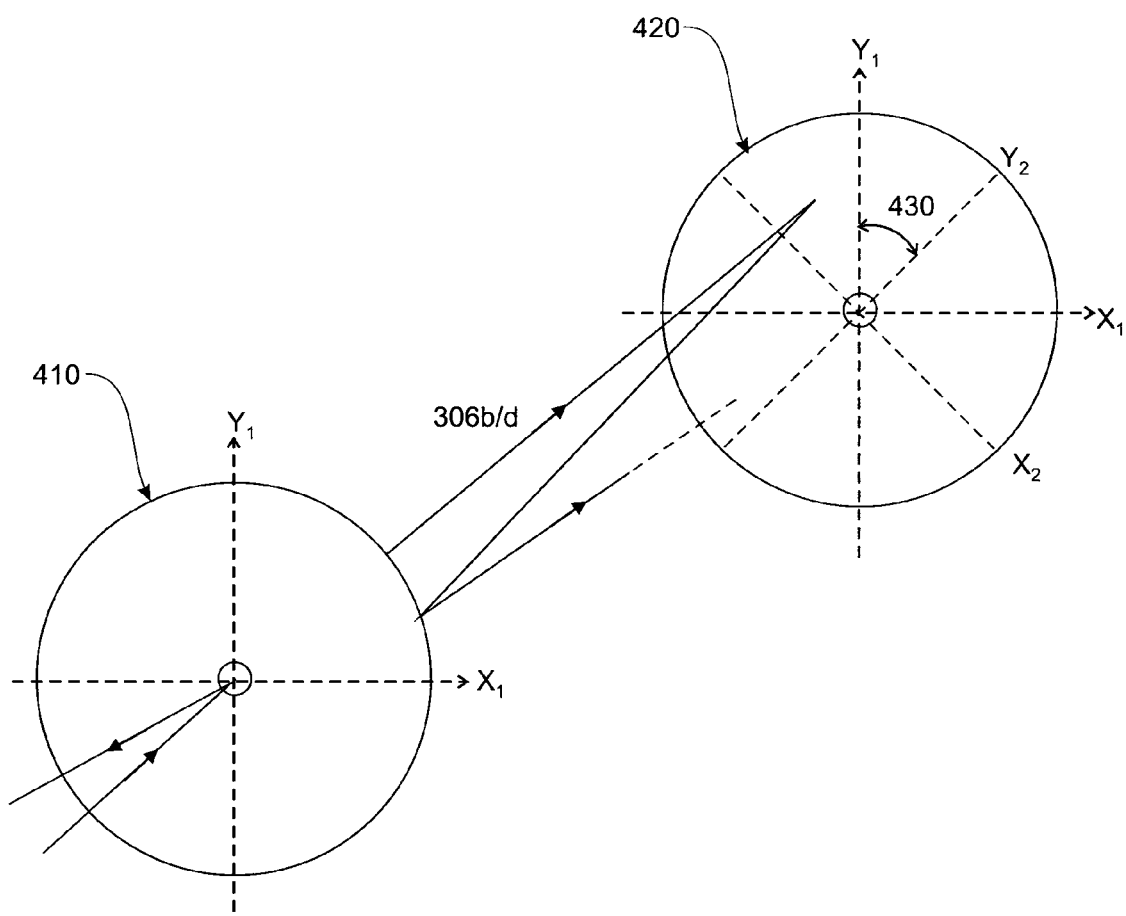
FIG. 17c is a diagram showing the rotation of the cylindrical concave mirrors of the optical system of FIG. 17a relative to each other.

With reference to FIGS. 17a-17c, another possible form of multi-pass cell that may be utilised in the optical system of the gas detector will be described. The arrangement of laser sources 302a-302d and optical detectors 304a,304c,304b/d are substantially the same as that described in example 2 although there is no reflecting planar mirror 314 for directing the exiting laser beam 306b,306d from the multi-pass cell toward the optical detector 304b/d. In this example, the multi-pass cell comprises two opposed cylindrical concave mirrors 410 and 420. In a similar manner to the multi-pass cell described in example 2, the laser beams 306b,306d enter the multi-pass cell through an input/output aperture located in the center of first cylindrical concave mirror 410 and are then reflected back and forth between the first 410 and the second 420 cylindrical concave mirrors multiple times before exiting the multi-pass cell through the input/output aperture 412 for detection at optical detector 304b/d.

Relative to the spherical concave mirror multi-pass cell of example 2, the cylindrical concave mirror multi-pass cell utilises more of the reflecting surface area of the mirrors in that the laser spot pattern takes up more of the reflecting surface area. Therefore, the cylindrical concave mirror multi-pass cell can have a reduced cell volume as well as mirror size for a given path length desired. Cylindrical concave mirrors have two principle axes, one along their planar direction and one perpendicular to this along the curved direction. With reference to FIGS. 17b and 17c, it will be appreciated by those skilled in the art that the cylindrical concave mirrors 410,420, at an appropriate spacing, may be rotated relative to one another to provide the desired laser beam reflection pattern and length for a re-entrant multi-pass cell (a cell having a single input/output aperture). In FIGS. 17b and 17c, axes X1 and X2 represent the curved axes of the respective mirrors 410 and 420, and axes Y1 and Y2 represent the planar axes of the respective mirrors 410 and 420. In one form, the second mirror 420 may be rotated by an angle 430 with respect to the first mirror 410. It will also be appreciated that the two opposed cylindrical concave reflecting surfaces 410 and 420 may be provided in a single cylinder having an internal reflecting surface if desired.

Specific Multi-Pass Cell Parameter Examples

Table 3 below sets out example parameters for the spherical concave mirror multi-pass cell explained in example 2 for two particular desired radiation transmission path lengths, namely 20.6 m and 30.0 m. The parameters are as follows:
Diameter=minimum mirror diameter in mm,
L=path length for the optical cell,
d=mirror separation,
f=mirror focal length (equal to the radius of curvature divided by 2),
N=number of passes of the laser beams, and
Hole width=maximum diameter (in mm) of the input/output aperture to prevent the beam from exiting the cell early.

TABLE 3

| | Path Length (L) | |
|---|---|---|
| | 20.6 m | 30.0 m |
| Diameter | 25 mm | 25 mm |
| d | 170.58 mm | 154.76 mm |
| f | 90 mm | 80 mm |
| N | 120 | 192 |
| Hole width | 1.4 mm | 1.4 mm |

Table 4 below sets out example parameters for the cylindrical concave mirror multi-pass cell explained in example 4 for two particular desired radiation transmission path lengths, namely 20.8 m and 31.0 m.

TABLE 4

| | Path Length (L) | |
|---|---|---|
| | 20.8 m | 31.0 m |
| Diameter | 40 mm | 40 mm |
| d | 138.48 mm | 156.15 mm |
| f | 120 mm | 140 mm |
| N | 150 | 198 |
| Hole width | 2.5 mm | 2.5 mm |

Laser Sources, Optical Detectors and Drivers

It will be appreciated that alternative arrangements of laser sources and optical detectors may be used in other forms of the gas detector. The types of laser sources used, for example DFBs or VCSELs, can be the same or can be mixtures of different types. In one alternative form, the gas detector may employ four laser diode and photodiode aligned pairs, each pair corresponding to a target wavelength of one of the target gases. In another alternative form, the gas detector may employ a single laser diode that is sequentially tunable to each of the four target wavelengths and a corresponding single photodiode. Further, it will be appreciated that multiple current divers may be utilised to drive multiple laser sources in alternative forms of the gas detector. For example, each laser source may have its own current driver or alternatively there may be two or more current drivers that are each arranged to drive two or more lasers sources. Also, multiple lock-in amplifiers may be provided if multiple optical detectors are used. Each laser may be controlled by individual temperature control signals or individual microcontrollers.

Further, it will be appreciated that the four lasers may be run continuously, rather than in a pulsed manner. To enable the different radiation signals to be identified at the detection end for processing, each laser may be modulated at different modulation frequencies. A single photodiode, having a broad wavelength detection range, may then be utilised at the detection end and the individual modulation frequencies may be used to "identify" the signals for gas concentration determination.

The foregoing description of the invention includes preferred forms thereof. Modifications may be made thereto without departing from the scope of the invention as defined by the accompanying claims.

The invention claimed is:

1. A gas detector that is arranged to sense the concentration levels of a plurality of target gases within a gas sample from an environment surrounding the detector, comprising:
   a laser source or sources that are arranged to transmit radiation through the gas sample at target wavelengths that correspond approximately to the optimum absorption wavelengths of each of the target gases;
   an optical detector or detectors that are arranged to sense the intensity of the radiation transmitted through the gas sample at each of the target wavelengths and generate representative output intensity signals for each of the target wavelengths; and
   a control system that is arranged to operate the laser source(s) and optical detector(s), the control system having one or more current drivers that are arranged to drive the laser source(s) with drive current signals that are modulated with a sine wave and a triangle wave such that the signals are simultaneously triangularly ramped and sinusoidally modulated to generate wavelength scanned, and frequency modulated, radiation at or about each of the target wavelengths, and wherein the control system generates representative concentration level information relating to each of the target gases within the gas sample based on the level of absorption of the radiation transmitted into the gas sample at each of the target wavelengths with reference to the representative output intensity signals from the optical detector(s) for each of the target wavelengths.

2. A gas detector according to claim 1 wherein the control system is arranged to determine absorption levels based on the intensity of the radiation received by the optical detector(s) relative to the intensity of the radiation transmitted by the laser source(s) at each of the target wavelengths.

3. A gas detector according to claim 1 wherein there are a plurality of laser sources, one for each target gas, such that each laser source is arranged to transmit radiation through the gas sample at a target wavelength that corresponds approximately to the optimum absorption wavelength of its respective target gas.

4. A gas detector according to claim 3 wherein the control system is arranged to control the current driver(s) to activate each laser source sequentially in a pre-determined pattern in a cyclical manner one at a time.

5. A gas detector according to claim 4 wherein the current driver(s) of the control system are arranged to drive the laser sources in a pre-determined pattern via pulsed drive currents that are triangularly ramped and sinusoidally modulated.

6. A gas detector according to claim 3 wherein the control system is arranged to control the current driver(s) to activate each laser source sequentially in a pre-determined pattern in a cyclical manner one at a time with respective current drive signals having different sinusoidal modulation frequencies and wherein the control system further comprises a lock-in-amplifier that is sequentially configured by a reference signal to amplify and filter the output intensity signal from the optical detector(s), the reference signal being based on the sinusoidal modulation frequency of the current drive signal of the laser source that is activated such that it changes in a synchronous manner to correspond to the activated laser source.

7. A gas detector according to claim 1 wherein the plurality of target gases comprises the four target gases oxygen, methane, carbon monoxide, and hydrogen sulphide, and wherein the gas detector comprises four laser sources, one for each target gas such that each laser source is arranged to transmit radiation at a target wavelength that corresponds approximately to the optimum absorption wavelength of its respective target gas.

8. A gas detector according to claim 7 comprising a first optical detector that is arranged to sense the intensity of radiation transmitted through the gas sample at the target wavelength of methane, carbon monoxide and hydrogen sulphide, and a second optical detector that is arranged to sense the intensity of the radiation transmitted through the gas sample at target wavelength of oxygen.

9. A gas detector according to claim 1 wherein the control system further comprises a single lock-in amplifier that is arranged to amplify and filter the output intensity signal(s) from the optical detector(s) at each of the target wavelengths, one target wavelength at a time to correspond with the radiation wavelengths transmitted by the laser source(s).

10. A gas detector according to claim 1 further comprising a gas space through which a gas sample from the environment may pass, the laser source(s) and optical detector(s) being arranged about the gas space such that the laser source(s) transmit radiation through the gas sample in the gas space for detection by optical detector(s), and wherein the gas space comprises an optical system and wherein the radiation at one or more of the target wavelengths is indirectly transmitted from the laser source(s) to the optical detector(s) via the optical system, the optical system being arranged to modify and increase the radiation transmission path length at those target wavelengths relative to a direct transmission through the gas space.

11. A gas detector according to claim 10 wherein the optical system in the gas space comprises a multi-pass cell having an input aperture through which radiation from the laser source(s) enters the cell and an output aperture through which the radiation exits the cell for detection by the optical detector(s), the cell further comprising reflecting surfaces that are arranged to reflect the radiation back and forth within the cell multiple times to extend the radiation transmission path length through the gas sample within the cell before the radiation exits the cell through the output aperture.

12. A gas detector according to claim 1 wherein the gas detector is in the form of a hand-held device having a housing within which the components are securely mounted and an aperture within the housing through which the gas sample from the environment may flow, and wherein the control system further comprises an output display for displaying the concentration levels of the target gases within the gas sample.

13. A gas detector that is arranged to sense the concentration levels of a target gas(es) within a gas sample from an environment surrounding the detector, comprising:
   a laser source(s) that is arranged to transmit radiation through the gas sample at a target wavelength(s) that corresponds approximately to the optimum absorption wavelength(s) of the target gas(es);
   an optical detector(s) that is arranged to sense the intensity of the radiation transmitted through the gas sample at the target wavelength(s) and generate a representative output intensity signal(s) for the target wavelength(s); and a control system that is arranged to operate the laser source(s) and optical detector(s), the control system having a current driver(s) that is arranged to drive the laser source(s) with a drive current signal(s) that is modulated with a sine wave and a triangle wave such that the signal(s) is simultaneously triangularly ramped and sinusoidally modulated to generate wavelength scanned, and frequency modulated, radiation at or about the target wavelength(s), and wherein the control system generates representative concentration level information relating to the target gas(es) within the gas sample based on the level of absorption of the radiation transmitted into the gas sample at the target wavelength(s) with reference to the representative output intensity signal(s) from the optical detector(s) for the target wavelength(s).

14. A gas detector that is arranged to sense the concentration levels of target gases oxygen, methane, carbon monoxide, and hydrogen sulphide, within a gas sample from an environment surrounding the detector, comprising:

four laser sources corresponding to the four target gases, each laser source being arranged to transmit radiation through the gas sample at or about a target wavelength that corresponds approximately to the optimum absorption wavelength of its respective target gas;

an optical detector or detectors that are arranged to sense the intensity of the radiation transmitted through the gas sample at each of the target wavelengths and generate representative output intensity signals for each of the target wavelengths;

a gas space through which the gas sample from the environment may flow, the laser sources and optical detector(s) being arranged about the gas space such that the laser sources transmit radiation through the gas sample in the gas space for detection by the optical detector(s);

an optical system located in the gas space into which the laser sources for carbon monoxide and hydrogen sulphide direct their respective radiation, the optical system being arranged to modify and increase the radiation transmission path length between the laser sources and optical detector(s) for the radiation relative to a direct transmission through the gas space such that the radiation transmission path length is in the range of 20 m-50 m for the radiation at the target wavelength of carbon monoxide and is in the range of 10 m-35 m for the radiation at the target wavelength of hydrogen sulphide; and a control system that is arranged to operate the laser sources and optical detector(s), and which generates representative concentration level information relating to each of the target gases within the gas sample based on the level of absorption of the radiation transmitted into the gas sample at each of the target wavelengths with reference to the representative output intensity signals from the optical detector(s) for each of the target wavelengths.

15. A gas detector according to claim 14 wherein the control system is arranged to determine absorption levels based on the intensity of the radiation received by the optical detector(s) relative to the intensity of the radiation transmitted by the laser source(s) at each of the target wavelengths.

16. A gas detector according to claim 14 wherein the laser sources transmitting radiation at the target wavelengths of oxygen and methane are arranged to transmit the radiation directly through the gas sample to the optical detector(s).

17. A gas detector according to claim 14 wherein the radiation transmission path length between the laser source transmitting at the target wavelength of oxygen and the optical detector(s) is in the range of 0.01 m-0.1 m.

18. A gas detector according to claim 14 wherein the radiation transmission path length between the laser source transmitting at the target wavelength for methane and the optical detector(s) is in the range of 0.05 m-0.2 m.

19. A gas detector according to claim 14 wherein the optical system in the gas space comprises a multi-pass cell having an input aperture through which radiation from the laser sources enters the cell and an output aperture through which the radiation exits the cell for detection by the optical detector(s), the cell further comprising reflecting surfaces that are arranged to reflect the radiation back and forth within the cell multiple times to extend the radiation transmission path length through the gas sample within the cell before the radiation exits the cell through the output aperture, and wherein the multi-pass cell of the optical system comprise two spaced-apart reflecting surfaces that are arranged to reflect the radiation entering the cell through the input aperture back and forth between the surfaces multiple times before directing the radiation to exit the cell through the output aperture.

20. A gas detector according to claim 19 wherein the multi-pass cell of the optical system is arranged to reflect the radiation within the cell in a zig-zagged path in the cell before directing the radiation to exit the cell via the output aperture.

21. A gas detector according to claim 14 wherein the gas detector is in the form of a hand-held device having a housing within which the components are securely mounted and an aperture within the housing through which the gas sample from the environment may flow.

22. A portable hand-held gas detector that is arranged to sense the concentration levels of a plurality of target gases within a gas sample from an environment surrounding the detector, comprising:

a housing having a gas space through which the gas sample from the environment may flow;

a plurality of laser sources mounted within the housing about the gas space corresponding to the plurality of target gases, each laser source being arranged to transmit radiation through the gas sample in the gas space at or about a target wavelength that corresponds approximately to the optimum absorption wavelength of its respective target gas;

an optical detector or detectors mounted within the housing about the gas space that are arranged to sense the intensity of the radiation transmitted through the gas sample at each of the target wavelengths and generate representative output intensity signals for each of the target wavelengths; and a control system that is arranged to operate the laser sources and optical detector(s), the control system comprising:

one or more current drivers that are arranged to drive the laser sources with a pre-determined pattern of pulsed drive current signals so as to activate each laser source to transmit radiation at its respective target wavelength sequentially in a pre-determined pattern and cyclical manner one at a time; and a lock-in-amplifier that is arranged to sequentially amplify and filter that output intensity signals from the optical detector(s) at each of the target wavelengths one at a time in a synchronous manner according to the sequential activation of the corresponding laser sources, and wherein the control system generates and outputs representative concentration level information relating to each of the target gases within the gas sample based on the level of absorption of the radiation transmitted into the gas sample at each of the target wavelengths with reference to the filtered and amplified representative output intensity signals from the lock-in-amplifier for each of the target wavelengths.

23. A portable hand-held gas detector according to claim 22 wherein the control system is arranged to determine absorption levels based on the intensity of the radiation received by the optical detector(s) relative to the intensity of the radiation transmitted by the laser sources at each of the target wavelengths.

24. A portable hand-held gas detector according to claim 22 wherein the laser sources are arranged to transmit radiation in the infrared band.

25. A portable hand-held gas detector according to claim 22 wherein the target gases comprise any two or more of the target gases: oxygen, methane, carbon monoxide, hydrogen sulphide, ammonia, water, acetylene, carbon dioxide, nitrogen oxide, ethylene, and nitrogen dioxide.

26. A portable hand-held gas detector according to claim 22 comprising a single optical detector that is arranged to sense the intensity of radiation transmitted through the gas sample at all of the target wavelengths of the target gases.

27. A portable hand-held gas detector according to claim 22 wherein the current driver(s) of the control system are arranged to drive the laser sources using drive current signals that are modulated with a sine wave and a triangle wave such that the signals are simultaneously triangularly ramped and sinusoidally modulated.

28. A portable hand-held gas detector according to claim 22 wherein the current driver(s) of the control system are arranged to generate current drive signals in the form of pulses that are triangularly ramped and sinusoidally modulated.

29. A portable hand-held gas detector according to claim 28 wherein the control system is arranged to control the current driver(s) to activate each laser source with respective current drive signals having different sinusoidal modulation frequencies and wherein the lock-in-amplifier is sequentially configured by a reference signal to amplify and filter the output intensity signal(s) from the optical detector(s), the reference signal being based on the sinusoidal modulation frequency of the current drive signal of the laser source that is activated such that it changes in a synchronous manner to correspond to the activated laser source.

30. A portable hand-held gas detector according to claim 22 wherein the gas space comprises an optical system and wherein the radiation at one or more of the target wavelengths is indirectly transmitted from the laser source(s) to the optical detector(s) via the optical system, the optical system being arranged to modify and increase the radiation transmission path length at those target wavelengths relative to a direct transmission through the gas space.

* * * * *